United States Patent
Boss

(10) Patent No.: US 11,419,916 B2
(45) Date of Patent: Aug. 23, 2022

(54) METHODS AND COMPOSITIONS FOR INDUCING DIFFERENTIATION OF HUMAN BROWN ADIPOCYTE PROGENITORS

(71) Applicant: Energesis Pharmaceuticals, Inc., Cambridge, MA (US)

(72) Inventor: Olivier D. Boss, Boston, MA (US)

(73) Assignee: ENERGESIS PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 15/120,850

(22) PCT Filed: Feb. 24, 2015

(86) PCT No.: PCT/US2015/017392
§ 371 (c)(1),
(2) Date: Aug. 23, 2016

(87) PCT Pub. No.: WO2015/127474
PCT Pub. Date: Aug. 27, 2015

(65) Prior Publication Data
US 2016/0361386 A1    Dec. 15, 2016

Related U.S. Application Data

(60) Provisional application No. 61/966,496, filed on Feb. 24, 2014.

(51) Int. Cl.
*A61K 38/18* (2006.01)
*A61K 31/426* (2006.01)
(Continued)

(52) U.S. Cl.
CPC ........ *A61K 38/1825* (2013.01); *A61K 31/165* (2013.01); *A61K 31/166* (2013.01);
(Continued)

(58) Field of Classification Search
None
See application file for complete search history.

(56) References Cited

U.S. PATENT DOCUMENTS 6,242,563 B1   6/2001   Dong
8,455,204 B2   6/2013   Boss et al.
(Continued)

FOREIGN PATENT DOCUMENTS

CN   102105789   6/2011
CN   103517982   1/2014
(Continued)

OTHER PUBLICATIONS

Humphries et al., Aliment. Pharmacol. Ther. 13(Suppl. 3): 18-26 (1999).*
(Continued)

*Primary Examiner* — Erin M. Bowers
(74) *Attorney, Agent, or Firm* — Saliwanchik, Lloyd & Eisenschenk

(57) ABSTRACT

This disclosure relates to compositions and methods for recruiting brown adipocytes in vitro and in vivo from brown adipocyte progenitor cells found in human skeletal muscle. Methods for treating metabolic disease are also provided. Additionally, methods for treating hypothermia are provided. In some embodiments, the brown adipocyte recruiter is a human protein or peptide. In other embodiments the brown adipocyte recruiter may be a non-human protein or peptide. In still other embodiments, the brown adipocyte recruiter is a small molecule or natural product.

3 Claims, 15 Drawing Sheets
Specification includes a Sequence Listing.

(51) Int. Cl.

| | | |
|---|---|---|
| A61K 31/166 | (2006.01) | |
| A61K 31/5415 | (2006.01) | |
| A61K 31/165 | (2006.01) | |
| A61K 31/4745 | (2006.01) | |
| A61K 31/506 | (2006.01) | |
| A61K 31/44 | (2006.01) | |
| A61K 31/5575 | (2006.01) | |
| A61K 31/353 | (2006.01) | |
| A61K 38/10 | (2006.01) | |
| A61K 38/22 | (2006.01) | |
| A61K 38/19 | (2006.01) | |
| A61K 38/20 | (2006.01) | |

(52) U.S. Cl.
CPC .......... *A61K 31/353* (2013.01); *A61K 31/426* (2013.01); *A61K 31/44* (2013.01); *A61K 31/4745* (2013.01); *A61K 31/506* (2013.01); *A61K 31/5415* (2013.01); *A61K 31/5575* (2013.01); *A61K 38/105* (2013.01); *A61K 38/185* (2013.01); *A61K 38/195* (2013.01); *A61K 38/204* (2013.01); *A61K 38/22* (2013.01); *A61K 38/2278* (2013.01)

(56) References Cited

U.S. PATENT DOCUMENTS

| | | | |
|---|---|---|---|
| 9,410,945 | B2 | 8/2016 | Boss et al. |
| 2001/0024824 | A1* | 9/2001 | Moss .................. C12N 5/0677 435/366 |
| 2005/0009739 | A1 | 1/2005 | Wang et al. |
| 2005/0019824 | A1* | 1/2005 | Alderson ............... C07K 14/50 435/6.16 |
| 2008/0253996 | A1* | 10/2008 | Boschert ............. A61K 38/195 424/85.6 |
| 2011/0104133 | A1 | 5/2011 | Tseng et al. |
| 2011/0117066 | A1 | 5/2011 | Ailhaud et al. |
| 2011/0130385 | A1 | 6/2011 | De Lera Ruiz et al. |
| 2013/0303573 | A1 | 11/2013 | Boss et al. |

FOREIGN PATENT DOCUMENTS

| | | | |
|---|---|---|---|
| EP | 2397152 | A2 | 12/2011 |
| JP | 10330284 | A | 12/1998 |
| JP | 10330285 | A | 12/1998 |
| JP | 2010130968 | A | 6/2010 |
| WO | 2004096853 | A1 | 11/2004 |
| WO | 2005/037232 | | 4/2005 |
| WO | 2009151541 | A1 | 12/2009 |
| WO | WO 2009/151541 | * | 12/2009 |
| WO | WO 2011/054001 | | 5/2011 |
| WO | 2011/126790 | | 10/2011 |
| WO | 2012/099999 | A2 | 7/2012 |
| WO | WO 2012/156968 | | 11/2012 |
| WO | 2013/071050 | A1 | 5/2013 |
| WO | 2013071063 | A1 | 5/2013 |
| WO | WO 2013/071063 | * | 5/2013 |
| WO | 2013137826 | | 9/2013 |
| WO | 2014026201 | | 2/2014 |

OTHER PUBLICATIONS

Stanford et al., J. Clin. Invest. 123(1): 215-223 (Jan. 2013).*
Ma et al., J. Mol. Cell Biol. 4: 88-96 (2012).*
Bohm et al., Gastroenterology 139: 1385-1396 (2010).*
Steiling et al., Oncogene 22: 4380-4388 (2003).*
Diane et al., J. Endocrinol. 222(3): 327-339 (2014).*
Donath et al., Diabetes 54(Suppl. 2): S108-S113 (2005).*
Movassat et al., J. Endocrinol. 195: 333-340 (2007).*
Marchetti et al., "Chapter 22: Pancreatic β-Cells in Human Type 2 Diabetes", Diabetes: An Old Disease, a New Insight, Landes Bioscience, 2013.*

Jin et al., Cardiovascular Res. 100: 481-491 (2013).*
International Search Report in International Application No. PCT/US2015/017392 dated Jun. 8, 2015.
Boss et al., "Recruitment of brown adipose tissue as a therapy for obesity-associated diseases", Frontiers in Endocrinology, 6, Feb. 2012, pp. 1-6.
Vegiopoulos et al., "Cyclooxygenase-2 Controls Energy Homeostasis in Mice by de Novo Recruitment of Brown Adipocytes", Science Magazine, vol. 328, May 28, 2010, pp. 1158-1161.
Extended European Search Report for European Patent Application No. PCT/US2010017392, dated Jun. 21, 2017.
Schulz, et al., "Identification of inducible brown adipocyte progenitors residing in skeletal muscle and white fat", PNAS, vol. 108, vol. 1, pp. 143-148, (2011).
Yun-Hee Lee et al., "Recent advance in brown adipose physiology and its therapeutic potential", Experimental & Molecular Medicine, vol. 46, e78, Feb. 21, 2014.
Lidell et al., "Brown Adipose Tissue and its Therapeutic Potential", Journal of Internal Medicine, vol. 276, No. 4, Oct. 2014, pp. 364-377.
Saito M, "Brown Adipose Tissue as a Therapeutic Target for Human Obesity", Obesity Research and Clinical Practice 2013 Elsevier LTD GBR, vol. 7, No. 6, Dec. 2013.
Fogari et al., "Comparison of the Effects of Valsartan and Felodipine on Plasma Leptin and Insulin Sensitivity in Hypertensive Obese Patients", Hyertension Research Clinical and Experimental, vol. 28, No. 3, Jan. 1, 2005, pp. 209-214.
Olivier Boss, et al., "Recruitment of Brown Adipose Tissue as a Therapy for Obesity-Associated Diseases," Frontiers in Endocrinology, vol. 3 Jan. 1, 2012, pp. 1-6.
Madsen et al., "UCP1 Induction during Recruitment of Brown Adipocytes in White Adipose Tissue is Dependent on Cyclooxygenase Activity," PLoS One, 2010, vol. 5, Iss. 6, e11391.
Zafrir, B., "Brown Adipose Tissue: Research Milestones of a Potential Player in Human Energy Balance and Obesity," Hormone and Metabolic Research, 2013, vol. 45, Iss 11, pp. 774-785.
King, "The use of animal models in diabetes research," Br J Pharmacol. Jun. 2012; 166(3): 877-894.
American Diabetes Association, "Diagnosis and Classification of Diabetes Mellitus", Diabetes Care Jan. 2014; 37 (Supplement 1): S81-S90.
Weir et al., "Five Stages of Evolving b-Cell Dysfunction During Progression to Diabetes", Diabetes, vol. 53, Supplement 3, Dec. 2004.
Zhang et al., "Receptor specificity of the fibroblast growth factor family", J Biol Chem. Jun. 9, 2006;281(23):15694-700.
Kim, J. et al. "Impact of Blockade of Histamine $H_2$ Receptors on Chronic Heart Failure Revealed by Retrospective and Prospective Randomized Studies" *Journal of the American College of Cardiology*, 2006, pp. 1378-1384, vol. 48, No. 7.
Masaki, T. et al. "The hypothalamic $H_1$ receptor: a novel therapeutic target for disrupting diurnal feeding rhythm and obesity" *TRENDS in Pharmacological Sciences*, May 2006, pp. 279-284, vol. 27, No. 5.
Mestre, T. A. et al. "Famotidine, a Histamine $H_2$ Receptor Antagonist, Does Not Reduce Levodopa-Induced Dyskinesia in Parkinson's Disease: A Proof-of-Concept Study" *International Parkinson and Movement Disorder Society*, Jun. 26, 2014, pp. 219-224.
Oh, J.-E. et al. "Inhibition of mouse brown adipocyte differentiation by second-generation antipsychotics" *Experimental and Molecular Medicine*, Sep. 2012, pp. 545-553, vol. 44, No. 9.
Støa-Birketvedt, G. et al. "$H_2$-receptor antagonist reduces food intake and weight gain in rats by non-gastric acid secretory mechanisms" *Acta Physiol Scand*, 1997, pp. 489-494, vol. 161.
Støa-Birketvedt, G. et al. "Cimetidine reduces weight and improves metabolic control in overweight patients with Type 2 diabetes" *International Journal of Obesity*, 1998, pp. 1041-1045, vol. 22.
Gray, S. L. et al. "Temperature-Sensitive Phenotype in Mice Lacking Pituitary Adenylate Cyclase-Activating Polypeptide" *Endocrinology*, pp. 3946-3954, vol. 143, No. 10.
Reglodi, D. et al. "Review on the Protective Effects of PACAP in Models of Neurodegenerative Diseases In Vitro and In Vivo" *Current Pharmaceutical Design*, 2011, pp. 962-972, vol. 17.

(56) References Cited

OTHER PUBLICATIONS

Extended European Search Report, Application No. 21193195.1, dated Apr. 7, 2022, pp. 1-32.

* cited by examiner

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
tcaaggggtt ggtaccttcc                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
cactaacgaa ggaccaacgg                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
ttccaggatc caagtcgcaa                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
actgccaaga ctgagtggtt                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic
```

-continued

```
<400> SEQUENCE: 5
caaatgctgg acccaacaca                                                     20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
tcactttgcc aaacaccaca                                                     20

<210> SEQ ID NO 7
<211> LENGTH: 22
<212> TYPE: DNA
<213> ORGANISM: Artificial Sequence
<220> FEATURE:
<223> OTHER INFORMATION: Synthetic

<400> SEQUENCE: 7
tcacaagaaa tgaccatggt tg                                                  22

<210> SEQ ID NO 8
<211> LENGTH: 22
<212> TYPE: DNA
<213> ORGANISM: Artificial Sequence
<220> FEATURE:
<223> OTHER INFORMATION: Synthetic

<400> SEQUENCE: 8
agcgattcct tcactgatac ac                                                  22

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
ccagaatggc atctctgtgt                                                     20
```

METHODS AND COMPOSITIONS FOR INDUCING DIFFERENTIATION OF HUMAN BROWN ADIPOCYTE PROGENITORS

CROSS REFERENCE TO RELATED APPLICATIONS

This application is a National Phase application of International Application No. PCT/US2015/017392, filed Feb. 24, 2015 which claims priority to and the benefit of U.S. Provisional Application No. 61/966,496 filed Feb. 24, 2014, the entire disclosure of both of which is incorporated herein by reference.

STATEMENT REGARDING FEDERALLY SPONSORED RESEARCH

This invention was made with government support under contract number 1R43DK099005-01 awarded by the Department of Health and Human Services. The government has certain rights in the invention.

TECHNICAL FIELD

The present disclosure relates to compositions and methods related to enhancing brown adipocytes, and/or brown adipocyte mass, in conditions such as type 2 diabetes, obesity, insulin-resistance, and dyslipidemia. Specifically, the present disclosure identifies and describes compounds that increase or promote the differentiation of brown adipose tissue (BAT) progenitor cells isolated from skeletal muscle into brown adipocytes. Further, the present disclosure identifies and describes compounds which interact with gene products involved in the regulation of brown adipocyte differentiation and/or mass. Still further, the present disclosure provides methods for the identification and therapeutic use of compounds for the prevention and treatment of type 2 diabetes, obesity, insulin-resistance, and dyslipidemia. The disclosure is useful for the study, prevention, and treatment of various metabolic diseases such as obesity, type 2 diabetes, insulin-resistance and dyslipidemia.

BACKGROUND

The epidemic of obesity is closely associated with increases in the prevalence of diabetes, hypertension, coronary heart disease, cancer and other disorders. The role of white adipose tissue is to store lipids, and it is associated with obesity. The role of brown adipose tissue ("BAT") is effectively the opposite. It is specialized in lipid combustion and the dissipation of energy as heat. Indeed, the brown adipocyte contains numerous mitochondria (in which cellular combustion occurs) and uniquely expresses uncoupling protein-1 ("UCP1"). UCP1 acts as an uncoupler of oxidative phosphorylation, resulting in dissipation of energy as heat. The sympathetic nervous system stimulates mitochondriogenesis and UCP1 expression and activity. BAT-associated thermogenesis in rodents is increased upon exposure to low temperature (e.g., preventing hypothermia) or as a result of overeating, burning excess absorbed fat and preventing weight gain. BAT, by modifying susceptibility to weight gain and by consuming large amounts of glucose, also improves insulin sensitivity. It therefore plays an important role in the maintenance of body temperature, energy balance and glucose metabolism.

Experiments with transgenic animals support the potential anti-obesity properties of BAT. For example, the genetic ablation of BAT has been reported to cause obesity, while genetic increase in the amount and/or function of BAT (and/or UCP1 expression) reportedly promotes a lean and healthy phenotype. Specifically, mice with a higher amount of BAT gain less weight and are more insulin-sensitive than control mice. Recently, ectopic BAT depots were evidenced in the mouse muscle, which have been shown to provide a genetic mechanism of protection from weight gain and metabolic syndrome.

Although UCP1 is reported to play a role in the control of energy balance in rodents and UCP1-expressing BAT is present in human neonates, it has long been thought that there was no physiologically relevant UCP1 expression in adult humans. Indeed, UCP1-expressing BAT was thought to disappear early in life, and adult humans were thought to be devoid of BAT. Recently however, numerous studies have demonstrated that BAT is indeed maintained in most adult humans, albeit at considerably lower levels than in neonates and children.

As such, a need exists to carefully identify and study ways to provide more BAT in the adult body and/or stimulate UCP1 expression, for the study, prevention and treatment of various metabolic diseases such as obesity, type 2 diabetes, insulin-resistance, dyslipidemia and type 1 diabetes.

Applicants previously identified the presence of cells in various tissues that are capable of differentiating into brown adipocytes in e.g., PCT Publication No. WO2009151541 and WO2013071063, the entire disclosures of both of which are incorporated herein by reference. However, a need exists for agents (e.g., compounds, proteins, biologicals, and the like) that can, for example, induce the expression of the UCP1 gene, promote the differentiation of BAT progenitor cells into brown adipocytes in vitro, promote the differentiation of BAT progenitor cells to brown adipocytes in vivo, or combinations of these activities.

SUMMARY

The present disclosure provides compositions for recruiting or producing brown adipocytes in vitro and in vivo from BAT progenitor cells found in human skeletal muscle. These agents, or combinations thereof, can be used to promote the differentiation of BAT progenitor cells into brown adipocytes and/or induce the expression of UCP1, FABP4 (aP2), PPARγ2, mtTFA, PGC-1α, and/or COX IV in BAT progenitor cells in vitro, in vivo, or both. Furthermore, these agents can be used to treat metabolic disease, including without limitation obesity, diabetes, insulin resistance, hyperlipidemia, and others conditions in a patient.

The present disclosure is based, in part, on the discovery that various proteins, peptides, and small molecules (collectively, agents) play an important role in the differentiation of BAT progenitor cells. In particular, it has been found that the various agents disclosed herein markedly induce differentiation of BAT progenitor cells isolated from human skeletal muscle into mature, functional brown adipocytes. Treatment of these BAT progenitor cells with one or more of these various agents triggers commitment of these cells to brown adipocyte differentiation. In some cases, treatment with an agent for a period of time (e.g., a few hours, 1 day, 2 days, 3 days, or shorter or longer) prior to the introduction of an adipogenic medium results in brown adipocyte differentiation. In other cases, treatment with an agent contemporaneously with, and/or after the introduction of adipogenic medium results in brown adipocyte differentiation.

Since brown adipose tissue (BAT) is specialized for energy expenditure, the agents described herein are useful for the treatment of obesity and related disorders, such as diabetes. The agents can also be used to decrease fat stores in subjects including food animals, e.g., to improve the quality of the meat derived therefrom.

Accordingly, in one aspect, the disclosure features a method of treating a subject, e.g., decreasing fat stores or weight in a subject such as a human. The method includes administering to the subject an effective amount of an agent or combination of agents disclosed herein.

In a further aspect, the disclosure features a method of treating a subject in need of decreasing fat stores or weigh, by administering a population of agent-activated BAT progenitor cells, wherein said population of agent-activated progenitor cells undergo brown adipogenesis. The method can optionally include identifying a subject in need of decreasing fat stores or weight.

In a further aspect, the disclosure includes a method of enhancing insulin sensitivity in a subject, e.g., a subject that is insulin-resistant. The method includes administering to the subject an agent and/or a population of agent-activated BAT progenitor cells, wherein said population of agent-activated BAT progenitor cells undergo brown adipogenesis. The method can optionally include identifying a subject in need of enhanced insulin sensitivity.

In another aspect, the disclosure features a method of modulating brown adipose tissue function or development, e.g., promoting BAT adipogenesis, in a subject. The method includes administering to the subject an agent and/or a population of agent-activated BAT progenitor cells, wherein said population of agent-activated progenitor cells undergo brown adipogenesis.

In some embodiments, methods described herein can include implanting a population of agent-activated BAT progenitor cells into a subject. The agent-activated cells can be implanted directly or can be administered in a scaffold, matrix, or other implantable device to which the cells can attach (examples include carriers made of, e.g., collagen, fibronectin, elastin, cellulose acetate, cellulose nitrate, polysaccharide, fibrin, gelatin, self-assembling small peptides, and combinations thereof). In general, the methods include implanting a population of agent-activated BAT progenitor cells comprising a sufficient number of cells to promote increased brown adipocyte mass in the subject, e.g., to increase the amount of brown adipocytes in the subject by at least 1%, e.g., 2%, 5%, 7%, 10%, 15%, 20%, 25% or more.

In some embodiments, the methods include evaluating the level of BAT adipogenesis in a subject, by contacting isolated BAT progenitor cells from a subject with one or more of the agents disclosed herein. BAT differentiation can be evaluated by measuring any of, e.g., a BAT marker, such as uncoupling protein (UCP), e.g., UCP1, expression; BAT morphology (e.g., using visual, e.g., microscopic, inspection of the cells); or BAT thermodynamics, e.g., cytochrome oxidase activity, Na+-K+-ATPase enzyme units, or other enzymes involved in BAT thermogenesis.

In general, the subject can be a mammal. In some embodiments, the subject is a human subject, e.g., an obese human subject. In some embodiments, the subject is a non-human mammal, e.g., an experimental animal, a companion animal, or livestock, e.g., a cow, pig, or sheep that is raised for food. Generally, where a protein or peptide is used to recruit brown adipocytes from BAT progenitor cells, the protein or peptide will be from the same or related species as the subject, e.g., human, cat, dog, cow, pig, or sheep. The protein or peptide can also be heterologous to the subject.

In some embodiments, the methods include evaluating the subject for one or more of: weight, white adipose tissue stores, brown adipose tissue stores, adipose tissue morphology, insulin levels, insulin metabolism, glucose levels, thermogenic capacity, and cold sensitivity. The evaluation can be performed before, during, and/or after the administration of the agent and/or agent-activated BAT progenitor cells. For example, the evaluation can be performed at least 1 day, 2 days, 4 days, 7 days, 14 days, 21 days, 30 days or more or less before and/or after the administration.

In some embodiments, the methods include one or more additional rounds of treatment with an agent or implantation of agent-activated BAT progenitor cells, e.g., to increase brown adipocyte mass, e.g., to maintain or further reduce obesity in the subject.

In some embodiments where a protein or peptide agent is used, BAT progenitor cells can be genetically engineered to express increased levels of such protein or peptide, either stably or transiently. The cells can be, e.g., cultured mammalian cells, e.g., human cells. The expressed recombinant protein or peptide used will generally be of the same or related species as the BAT progenitor cells, e.g., a human protein or peptide expressed in human cells. The recombinant protein or peptide can also be heterologous to the BAT progenitor cells.

In a further aspect, the present disclosure provides use of one or more agents disclosed herein, for promoting differentiation of BAT progenitor cells into brown adipocytes and/or inducing expression of UCP1, FABP4 (aP2), PPARγ2, mtTFA, PGC-1α, and/or COX IV in BAT progenitor cells in vitro, in vivo, or both.

Also provided herein is use of one or more agents disclosed herein, for the treatment of one or more diseases or conditions selected from overweight, obesity, insulin resistance, diabetes, hyperinsulinemia, hypertension, hyperlipidemia, hepatosteatosis, fatty liver, non-alcoholic fatty liver disease, hyperuricemia, polycystic ovarian syndrome, acanthosis nigricans, hyperphagia, endocrine abnormalities, triglyceride storage disease, Bardet-Biedl syndrome, Laurence-Moon syndrome, Prader-Willi syndrome, neurodegenerative diseases, and Alzheimer's disease. Methods for treating the foregoing diseases are also provided, comprising administering one or more agents disclosed herein to a subject in need thereof.

A further aspect relates to a pharmaceutical composition, comprising one or more agents disclosed herein, and a pharmaceutically acceptable excipient, diluent or carrier.

One particular aspect relates to use of an agent for recruiting brown adipocytes from BAT progenitor cells isolated from human skeletal muscle, wherein the agent is selected from one or more of:

an antihistamine such as Famotidine;

an antidopaminergic such as Tiapride hydrochloride or Thiethylperazine or Spiperone;

a ligand of tubulin such as Colchicine;

a Rauwolfia alkaloid or derivative such as Reserpine or Syrosingopine;

a potassium channel ligand such as Minoxidil;

an antagonist of calcium channels such as Felodipine; Probenecid;

a derivative of prostaglandin F2 (PGF2) such as 9β,11α-PGF2 or 9α,11β-PGF2;

a peptide derived from Pituitary adenylate cyclase-activating polypeptide (PACAP) gene such as the PACAP Propeptide of 55 aa (aa 25-79);

a flavonoid such as kaempferol;

a fibroblast growth factor (FGF) such as FGF7 or FGF10 or FGF13;

a transient receptor potential melastatin 8 (TRPM8) ligand such as menthol or icilin;
bombesin;
stromal cell-derived factor 1 (SDF-1) such as isoform SDF-1γ;
a cyclooxygenase inhibitor such as Diflunisal;
a biguanide such as Metformin;
a phosphodiesterase inhibitor such as a PDE3 inhibitor such as siguazodan;
a stimulator of soluble guanylate cyclase (sGC) such as riociguat;
b-type natriuretic peptide (BNP);
ciliary neurotrophic factor (CNTF);
interleukin-6 (IL-6);
orexin B; and
an α2 adrenergic receptor agonist such as Guanfacine hydrochloride.

In some embodiments, the agent is selected from one or more of:
an antihistamine such as Famotidine;
an antidopaminergic such as Tiapride hydrochloride or Thiethylperazine;
a ligand of tubulin such as Colchicine;
a Rauwolfia alkaloid or derivative such as Reserpine or Syrosingopine;
a potassium channel ligand such as Minoxidil;
an antagonist of calcium channels such as Felodipine;
Probenecid;
a derivative of prostaglandin F2 (PGF2) such as 9β,11α-PGF2 or 9α,11β-PGF2;
a peptide derived from Pituitary adenylate cyclase-activating polypeptide (PACAP) gene such as the PACAP Propeptide of 55 aa (aa 25-79);
a flavonoid such as kaempferol;
a fibroblast growth factor (FGF) such as FGF7 or FGF10;
a transient receptor potential melastatin 8 (TRPM8) ligand such as menthol or icilin;
bombesin;
stromal cell-derived factor 1 (SDF-1) such as isoform SDF-1γ; and
a cyclooxygenase inhibitor such as Diflunisal.

In certain embodiments, the agent is capable of inducing expression of UCP1, FABP4 (aP2), PPARγ2, mtTFA, PGC-1α, and/or COX IV in the BAT progenitor cells in vitro, in vivo, or both.

In some embodiments, the agent can have one or more biological activities selected from the group consisting of:
(a) causing an increase or decrease in one or more of the following: Beta-3 adrenergic receptor (β3-AR), Solute carrier family 2, facilitated glucose transporter member 4 (SLC2A4), Elongation of very long chain fatty acids protein 3 (ELOVL3), CD36 antigen, Type II iodothyronine deiodinase (DIO2), BMP5, BMP6, FGF7, FGF10, FGF13, FGF21, Fatty acid binding protein 7 (FABP7), CXCL12, Atypical chemokine receptor 3 (ACKR3), Insulin-like growth factor-binding protein 4 (IGFBP4), Pituitary adenylate cyclase-activating polypeptide (PACAP), Adenylate cyclase 4 (ADCY4), Cell death activator CIDE-A (CIDEA), secreted frizzled-related protein 1 (SRFP1), SRFP2, brain-derived neurotrophic factor (BDNF), Vascular endothelial growth factor D (VEGF-D), Transforming growth factor beta-2 (TGFB2), cAMP-specific 3',5'-cyclic phosphodiesterase 4B (PDE4B), cAMP-specific 3',5'-cyclic phosphodiesterase 4D (PDE4D), High affinity cAMP-specific 3',5'-cyclic phosphodiesterase 7A (PDE7A), and cAMP-specific 3',5'-cyclic phosphodiesterase 7B (PDE7B);
(b) causing an increase in thermogenesis in brown adipose tissue and/or skeletal muscle tissue;
(c) causing an increase in insulin sensitivity of skeletal muscle, white adipose tissue, or liver;
(d) causing an increase in glucose tolerance;
(e) causing an increase in basal respiration, maximal respiration rate, or uncoupled respiration;
(f) causing an increase in metabolic rate; and
(g) causing a decrease in hepatosteatosis.

In certain embodiments, the agent can cause an increase or decrease in one or more of the following: Beta-3 adrenergic receptor (β3-AR), Solute carrier family 2, facilitated glucose transporter member 4 (SLC2A4), Elongation of very long chain fatty acids protein 3 (ELOVL3), CD36 antigen, and Type II iodothyronine deiodinase (DIO2).

In some embodiments, the agent is capable of modulating a metabolic response in a subject or preventing or treating a metabolic disorder in a subject. The metabolic disorder can, in some embodiments, be one or more of obesity, type II diabetes, insulin resistance, hyperinsulinemia, hypertension, hyperlipidemia, hepatosteatosis, fatty liver, non-alcoholic fatty liver disease, hyperuricemia, polycystic ovarian syndrome, acanthosis nigricans, hyperphagia, endocrine abnormalities, triglyceride storage disease, Bardet-Biedl syndrome, Laurence-Moon syndrome, Prader-Willi syndrome, neurodegenerative diseases, and Alzheimer's disease.

Another aspect relates to a method of promoting brown adipogenesis in a subject in need thereof, the method comprising administering to the subject an agent selected from one or more of agents disclosed herein. The method in some embodiments can further include modulating a metabolic response in the subject and/or preventing or treating a metabolic disorder in the subject. The metabolic disorder may be one or more of obesity, type II diabetes, insulin resistance, hyperinsulinemia, hypertension, hyperlipidemia, hepatosteatosis, fatty liver, non-alcoholic fatty liver disease, hyperuricemia, polycystic ovarian syndrome, acanthosis nigricans, hyperphagia, endocrine abnormalities, triglyceride storage disease, Bardet-Biedl syndrome, Laurence-Moon syndrome, Prader-Willi syndrome, neurodegenerative diseases, and Alzheimer's disease. In certain embodiments, the method further includes contacting a cell of the subject with the agent, and optionally transplantation of said cell into the subject after said contacting step. The cell in some embodiments can be a BAT progenitor cell isolated from human skeletal muscle. The cell can be positive for CD34 and/or negative for CD31.

Unless otherwise defined, all technical and scientific terms used herein have the same meaning as commonly understood by one of ordinary skill in the art to which this disclosure belongs. Methods and materials are described herein for use in the present disclosure; other suitable methods and materials known in the art can also be used. The materials, methods, and examples are illustrative only and not intended to be limiting. All publications, patent applications, patents, database entries, and other references mentioned herein are incorporated by reference in their entirety. In case of conflict, the present specification, including definitions, will control.

BRIEF DESCRIPTION OF THE DRAWINGS

FIG. 23A: Vehicle (DMSO). FIG. 23B: Rosiglitazone. FIG. 23C: BMP7. FIG. 23D: Diflunisal. FIG. 23E: Syrosingopine. FIG. 23F: Kaempferol. FIG. 23G: Probenecid. FIG. 23H: Tiapride.

DETAILED DESCRIPTION

Figure 1:
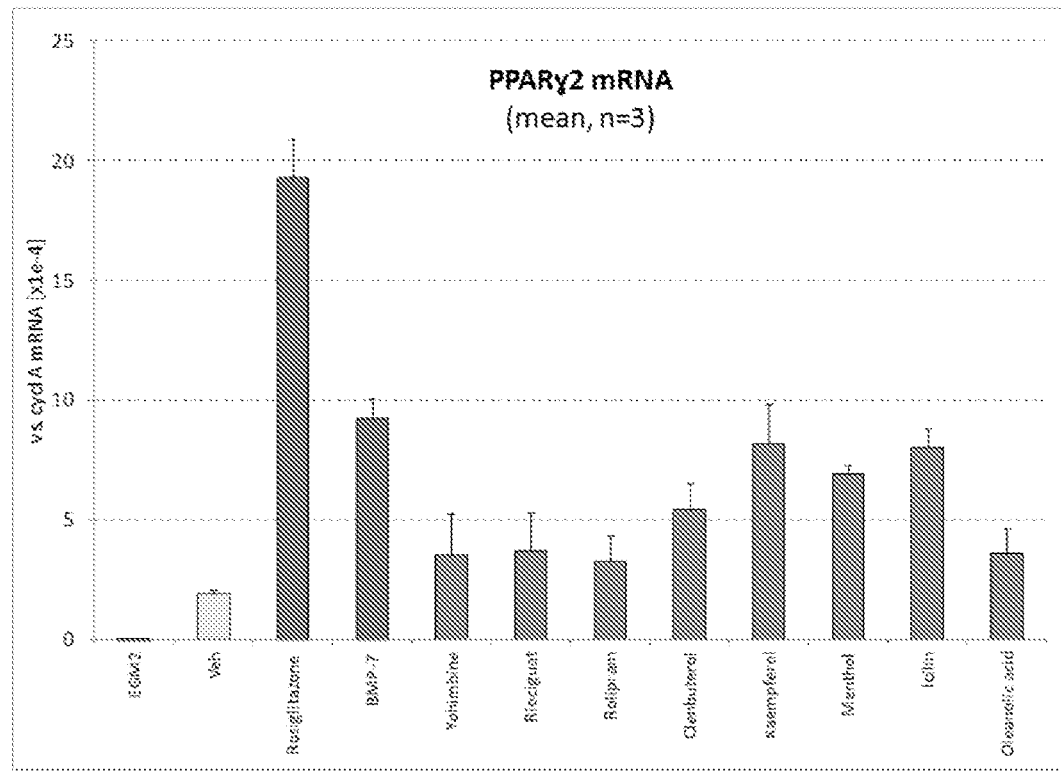
FIG. 1 shows effects of various agents (incubated with brown adipocyte progenitor cells at day-3 to d0 and d0 to d3) on the expression of PPARγ2 mRNA.

As used herein, "agent-activated" means that the BAT progenitor cell or cells have been treated with one or more agents as described herein and are at least partially committed to differentiate into brown adipocytes. The cells can be autologous, allogeneic, or xenogeneic. "Brown adipogenesis" means generation of brown adipocytes from BAT progenitor cells in vivo, in vitro, or partially in vivo and partially in vitro. It should be noted that brown adipogenesis may be induced, i.e., the so-called "BAT progenitor cells" before induction by, e.g., one or more agents disclosed herein, was not necessarily committed to differentiate into brown adipocytes and may be reprogrammed or transdifferentiate into brown adipocytes from a stem cell or a somatic cell. "Recruiting brown adipocytes" means promoting or enhancing differentiation of BAT progenitor cells into brown adipocytes, and/or increasing the amount or concentration of brown adipocytes, in vivo and/or in vitro.

Provided herein are agents (e.g., compounds, proteins, biologicals, and the like) that can promote the differentiation of BAT progenitor cells into brown adipocytes and/or induce the expression of the UCP1 gene in vitro, in vivo, or both. Such agents can be identified by screening compounds, proteins, biologicals, and the like. For example, in some embodiments BAT progenitor cells (e.g., those isolated from human skeletal muscle) can be used to screen agents for the ability to induce expression of the UCP1 gene and/or differentiation of the BAT progenitor cells into brown adipocytes. Agents identified in this manner can be used for a variety of research, diagnostic and therapeutic purposes, including, for example, treatment of metabolic diseases such as obesity, type 2 diabetes, insulin-resistance, dyslipidemia, and the like. In some embodiments, an agent identified by an assay according to the present disclosure is optimized for improvement of its physico-chemical and/or pharmacokinetic properties.

Expression of UCP1, FABP4 (aP2), PPARγ2, mtTFA, PGC-1α, and/or COX IV in BAT progenitor cells in vitro and in vivo can be enhanced according to methods provided in the present disclosure. In some embodiments, exposure to adipogenic media can be used to stimulate increased expression of UCP1, FABP4 (aP2), PPARγ2, mtTFA, PGC-1α, and/or COX IV in BAT progenitor cells.

Accordingly, in some embodiments the following agents, or combinations thereof, can be used to promote the differentiation of BAT progenitor cells into brown adipocytes and/or induce the expression of UCP1, FABP4 (aP2), PPARγ2, mtTFA, PGC-1α, and/or COX IV in BAT progenitor cells in vitro, in vivo, or both: a PDE3 inhibitor (e.g., siguazodan), a PDE4 inhibitor (e.g., rolipram), a derivative of prostaglandin F2 (PGF2) such as 9β,11α-prostaglandin F2 or 9α,11β-prostaglandin F2, a pepdide derived (e.g., a portion) from the Pituitary adenylate cyclase-activating polypeptide (PACAP, ADCYAP1, UniProt P18509) gene such as the PACAP Propeptide of 55 aa (aa 25-79), BDNF (brain-derived neurotrophic factor), a TGR5 agonist such as oleanolic acid, BMP-7, a flavonoid such as kaempferol (KMP, CAS number 520-18-3), a stimulator of soluble guanylate cyclase (sGC) such as riociguat (BAY 63-2521, CAS 625115-55-1), fibroblast growth factors (such as FGF7 (fibroblast growth factor-7, KGF, keratinocyte growth factor), FGF10 (fibroblast growth factor-10, KGF-2, keratinocyte growth factor-2), or FGF13 (fibroblast growth factor-13)), BNP (b-type natriuretic peptide), a TRPM8 (CMRI) ligand such as menthol or icilin, a bombesin peptide such as from the toad (UniProt P84214), CNTF (ciliary neurotrophic factor, UniProt P05231), interleukin-6 (IL-6), orexin B, SDF-1γ (CXCL12), or Guanfacine hydrochloride.

Further, in other embodiments additional agents or combinations thereof that can be used to promote the differentiation of BAT progenitor cells into brown adipocytes and/or induce the expression of UCP1 include prostaglandin J2 (PGJ2), 24(S)-Hydroxycholesterol, forms of vitamin D such as 1,25-Dihydroxyvitamin D3 or 24,25-Dihydroxyvitamin D3, and a cyclooxygenase inhibitor such as Diflunisal.

In still other embodiments, additional agents or combinations thereof that can be used to promote the differentiation of BAT progenitor cells into brown adipocytes and/or induce the expression of UCP1 include bone morphogenetic proteins such as BMP5 (bone morphogenetic protein 5, UniProt P22003) and BMP6 (bone morphogenetic protein 6, UniProt P22004), Platelet-derived growth factor receptor-like protein (PDGFRL, UniProt Q15198), Vascular endothelial growth factor D (VEGF-D, FIGF, UniProt O43915), CYTL1 (cytokine-like protein 1, UniProt Q9NRR1), SCG2 (secretogranin-2, UniProt P13521), NPTX2 (neuronal pentraxin-2, UniProt P47972), OLFML2B (olfactomedin-like protein 2B, UniProt Q68BL8), TFPI2 (tissue factor pathway inhibitor 2, UniProt P48307), IFNE (interferon epsilon, UniProt Q86WN2), a Prostaglandin F2-α receptor (PTGFR, prostanoid FP receptor, UniProt P43088) ligand such as prostaglandin F2, CNTF (ciliary neurotrophic factor), Interleukin-6 (IL-6, UniProt P05231), Interleukin-15 (IL-15, UniProt P40933), CXCL12 ((chemokine (C-X-C motif) ligand 12), stromal cell-derived factor 1, SDF1, UniProt P48061 isoform SDF-1g/UniProt P48061-3), and/or a ligand of Atypical chemokine receptor 3 (ACKR3, CMKOR1, CXCR7, GPR159, RDC1, UniProt P25106) such as SDF1 (CXCL12).

In still further embodiments, other agents or combinations thereof that can be used to promote the differentiation of BAT progenitor cells into brown adipocytes and/or induce the expression of UCP1 include a biguanide such as Metformin, an antihistamine such as Famotidine, an antidopaminergic such as Tiapride hydrochloride, Spiperone, Thiethylperazine, a microtubule modulator such as Colchicine, a Rauwolfia alkaloid or derivative of such as Reserpine or Syrosingopine, a potassium channel ligand such as Minoxidil, Probenecid, or a calcium channel antagonist such as Felodipine.

In some embodiments, treatment of a subject, including a human subject, with one or a combination of agents shown here, results in an increase in the production of UCP1 mRNA or protein in the subject's skeletal muscle. For example, treatment of subjects with rosiglitazone can, in some embodiments, induce the appearance or differentiation of brown adipocytes in skeletal muscle, enhance expression of the UCP1 gene in existing brown adipocytes in or near skeletal muscle (between myofibers, at the surface of and/or adjacent to skeletal muscle tissue), or both. In some embodiments the appearance or differentiation of brown adipocytes in skeletal muscle can be induced in a subject suffering from a metabolic disease. The brown adipocytes can provide a glucose sink with high mitochondrial and cellular respiration and fatty acid oxidation rates, dissipating energy as heat (uncoupled oxidative phosphorylation). The subject metabolic rate can be enhanced, and a decrease in body weight can be induced. Induction of the appearance or differentiation of brown adipocytes can also yield improvements in insulin sensitivity, blood glucose homeostasis and cardiovascular disease risk factors. Brown adipocytes may further secrete factors that contribute to reaching a healthy energy balance and low body fat levels, increased insulin sensitivity and improved blood glucose homeostasis or cardiovascular health.

Accordingly, in some embodiments the agents disclosed herein, or combinations thereof, can be used for treatment of a subject, including a human subject. In some aspects, these agents may promote the differentiation of BAT progenitor cells into brown adipocytes. In other aspects these agents may induce the expression of UCP1, FABP4 (aP2), PPARγ2, mtTFA, PGC-1α, and/or COX IV in BAT progenitor cells in vitro, in vivo, or both.

In some aspects the treated metabolic disease may be obesity, type II diabetes, insulin resistance, hyperinsulinemia, hypertension, hyperlipidemia, hepatosteatosis, fatty liver, non-alcoholic fatty liver disease, hyperuricemia, polycystic ovarian syndrome, acanthosis nigricans, hyperphagia, endocrine abnormalities, triglyceride storage disease, Bardet-Biedl syndrome, Laurence-Moon syndrome, Prader-Willi syndrome, neurodegenerative diseases, and Alzheimer's disease.

In other embodiments, agents may be used to activate isolated, autologous BAT progenitor cells that are then used for treatment of a subject, including a human subject.

Identification of Molecular Pathways

Gene chip studies were performed to identify molecular pathways that play a role in the differentiation of CD31- progenitor cells into brown adipocytes and/or the induction of the expression of UCP1. CD31-cells were isolated from human skeletal muscle biopsies as described previously in WO2013071063 which is incorporated herein by reference, and were used in two studies: (1) cAMP study: CD31-cells were differentiated as described in WO2013071063 and incorporated herein by reference (Control) plus addition of vehicle (Control 1 sample) or cAMP (cAMP sample); and (2) Rosiglitazone study: CD31-cells were differentiated as described previously in WO2013071063 except that rosiglitazone was omitted from the adipogenic medium (Control 2 sample). Rosiglitazone was added only to the second sample (Rosiglitazone sample) in this study. As discussed above, these agents have been shown to promote the differentiation of CD31-cells into brown adipocytes and the expression of UCP1.

Total RNA was purified from these samples, and transcriptional profiles were assessed with Illumina Human WG-6 BeadChip (Expression Analysis, Inc., Durham, N.C.). Results were analyzed with Ingenuity Pathway Analysis 7.0 (trial version). These results were used to determine what molecular pathways are involved in the differentiation of CD31-cells into brown adipocytes, and, more importantly, what molecular targets can be used for the development of agents that promote the appearance of brown adipocytes and the expression of UCP1.

Based on this work, the following mechanisms and agents were found to promote brown adipocyte development from BAT progenitor cells: a PPARγ ligand (e.g., rosiglitazone), a PDE3 inhibitor (e.g., siguazodan), a PDE4 inhibitor (e.g., rolipram), BMP7 (bone morphogenetic protein 7, UniProt P18075), BMP5 (bone morphogenetic protein 5, UniProt P22003), BMP6 (bone morphogenetic protein 6, UniProt P22004), FGF7 (fibroblast growth factor-7, KGF, keratinocyte growth factor), FGF10 (fibroblast growth factor-10, KGF-2, keratinocyte growth factor-2), BNP (b-type natriuretic peptide), FGF13 (fibroblast growth factor-13), BDNF (brain-derived neurotrophic factor), a stimulator of soluble guanylate cyclase (sGC) (e.g., riociguat (BAY 63-2521, CAS 625115-55-1), a TRPM8 (CMRI) ligand (e.g., menthol, icilin), Platelet-derived growth factor receptor-like protein (PDGFRL, UniProt Q15198), Vascular endothelial growth factor D (VEGF-D, FIGF, UniProt O43915), CYTL1 (cytokine-like protein 1, UniProt Q9NRR1), SCG2 (secretogranin-2, UniProt P13521), NPTX2 (neuronal pentraxin-2, UniProt P47972), OLFML2B (olfactomedin-like protein 2B, UniProt Q68BL8), TFPI2 (tissue factor pathway inhibitor 2, UniProt P48307), IFNE (interferon epsilon, UniProt Q86WN2), and a Prostaglandin F2-α receptor (PTGFR, prostanoid FP receptor, UniProt P43088) ligand such as prostaglandin F2. Still other mechanisms/agents that were found to promote brown adipocyte development from BAT progenitor cells based on gene chip data include: a peptide derived from the Pituitary adenylate cyclase-activating polypeptide (PACAP, ADCYAP1, UniProt P18509) gene such as PACAP Propeptide of 55 aa (aa 25-79) (200 nM-2 µM), CNTF (ciliary neurotrophic factor), Interleukin-6 (IL-6, UniProt P05231), Interleukin-15 (IL-15, UniProt P40933), CXCL12 (chemokine (C-X-C motif) ligand 12), stromal cell-derived factor 1 (SDF1, UniProt P48061) isoform SDF-1g/UniProt P48061-3), and/or a ligand of Atypical chemokine receptor 3 (ACKR3, CMKOR1, CXCR7, GPR159, RDC1, UniProt P25106) such as SDF1 (CXCL12).

Screening of Potential Modulators of Human UCP1 mRNA

CD31-cells can be used as a tool to identify agents (e.g., compounds, proteins, biologicals, and the like) that induce the differentiation of these cells into brown adipocytes or modulate the expression of UCP1. For example, an RT-PCR based approach can be used to measure UCP1 mRNA levels which may be affected by certain agents.

This allows the identification of agents that can enhance the differentiation of CD31-cells into brown adipocytes and/or the expression of UCP1 by enhancing the transcription of the UCP1 gene and/or by stabilizing the UCP1 transcript.

Figure 2:
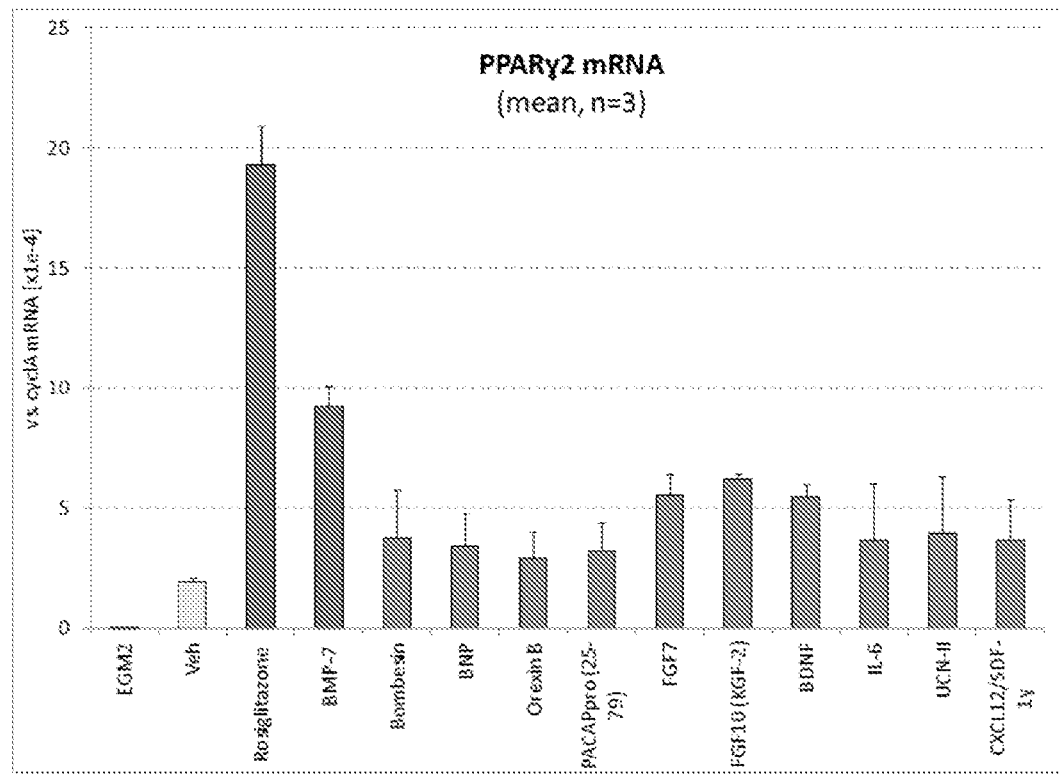
FIG. 2 shows effects of various agents (incubated with brown adipocyte progenitor cells at day-3 to d0 and d0 to d3) on the expression of PPARγ2 mRNA.
Figure 3:
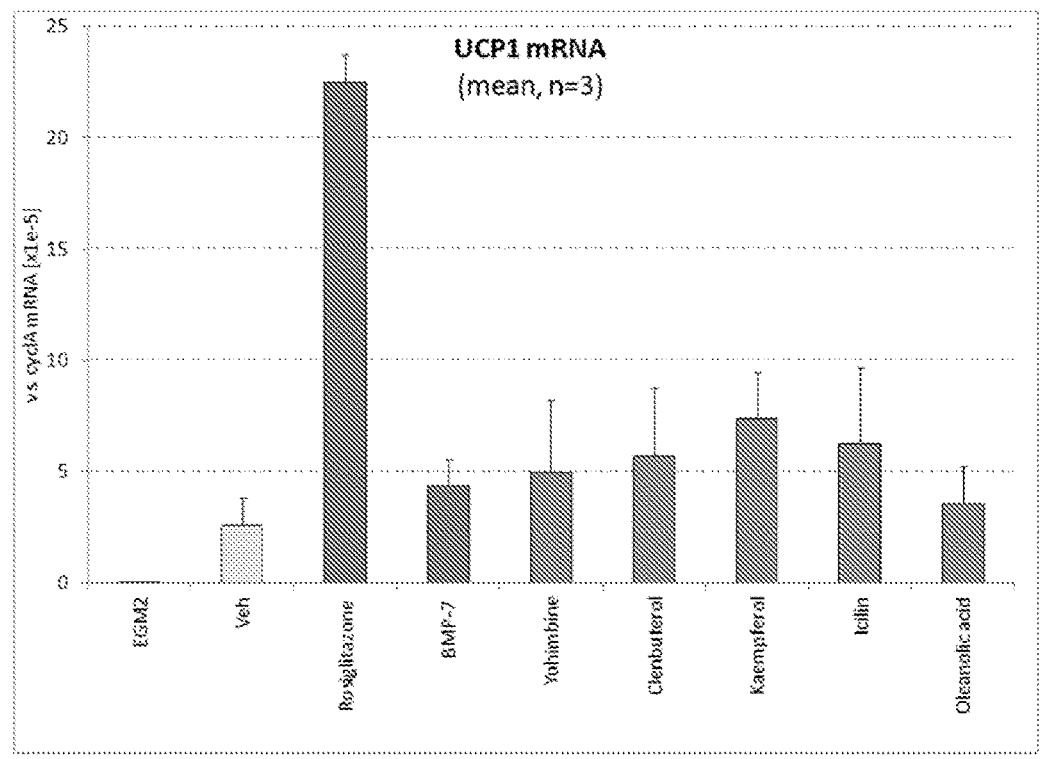
FIG. 3 shows effects of various agents (incubated with brown adipocyte progenitor cells at day-3 to d0 and d0 to d3) on the expression of UCP1 mRNA.
Figure 4:
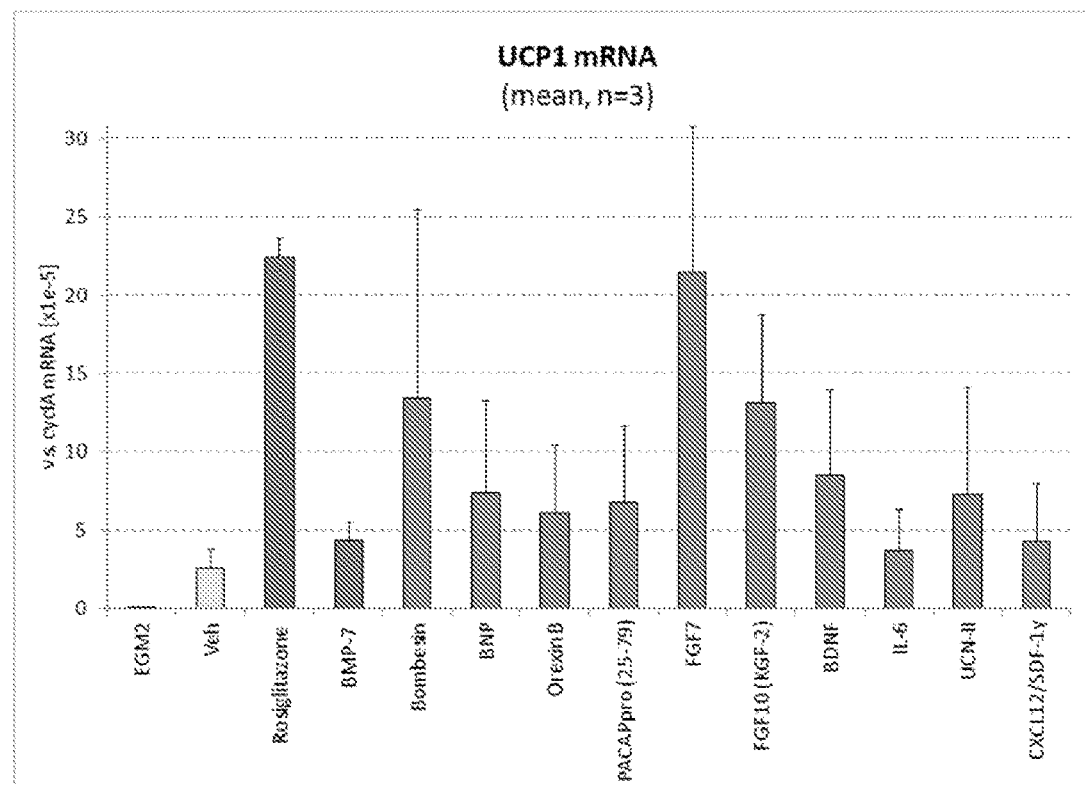
FIG. 4 shows effects of various agents (incubated with brown adipocyte progenitor cells at day-3 to d0 and d0 to d3) on the expression of UCP1 mRNA.
Figure 5:
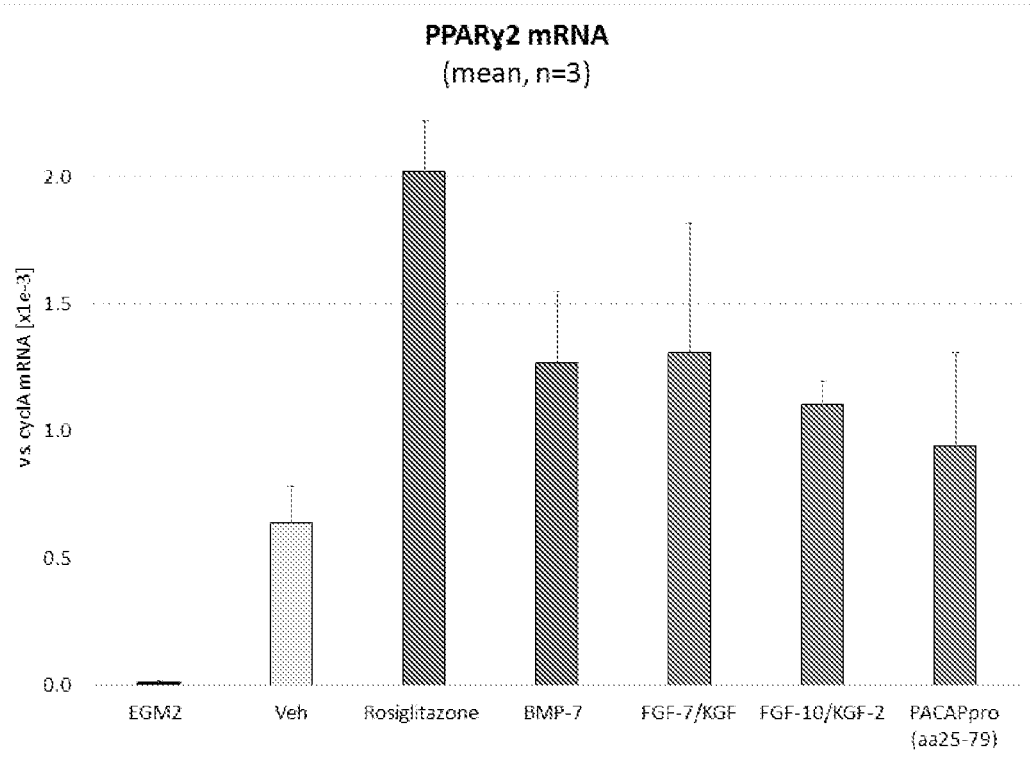
FIG. 5 shows effects of various agents (incubated with brown adipocyte progenitor cells at day-3 to d0) on the expression of PPARγ2 mRNA.
Figure 6:
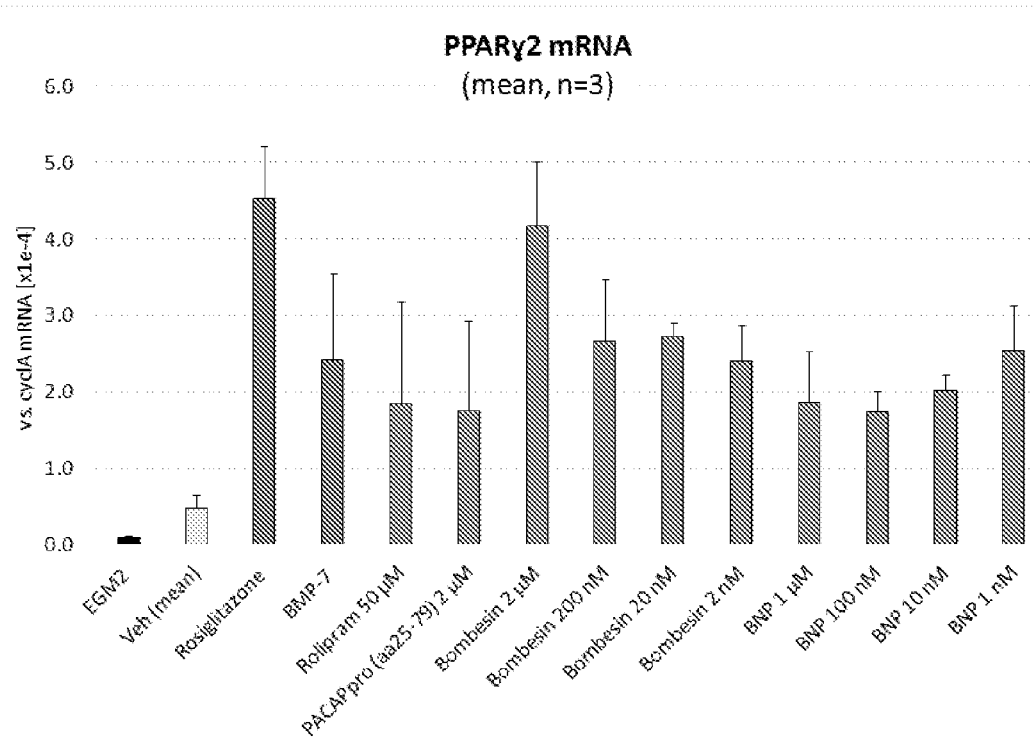
FIG. 6 shows effects of various agents (incubated with brown adipocyte progenitor cells at day-3 to d0) on the expression of PPARγ2 mRNA.
Figure 7:
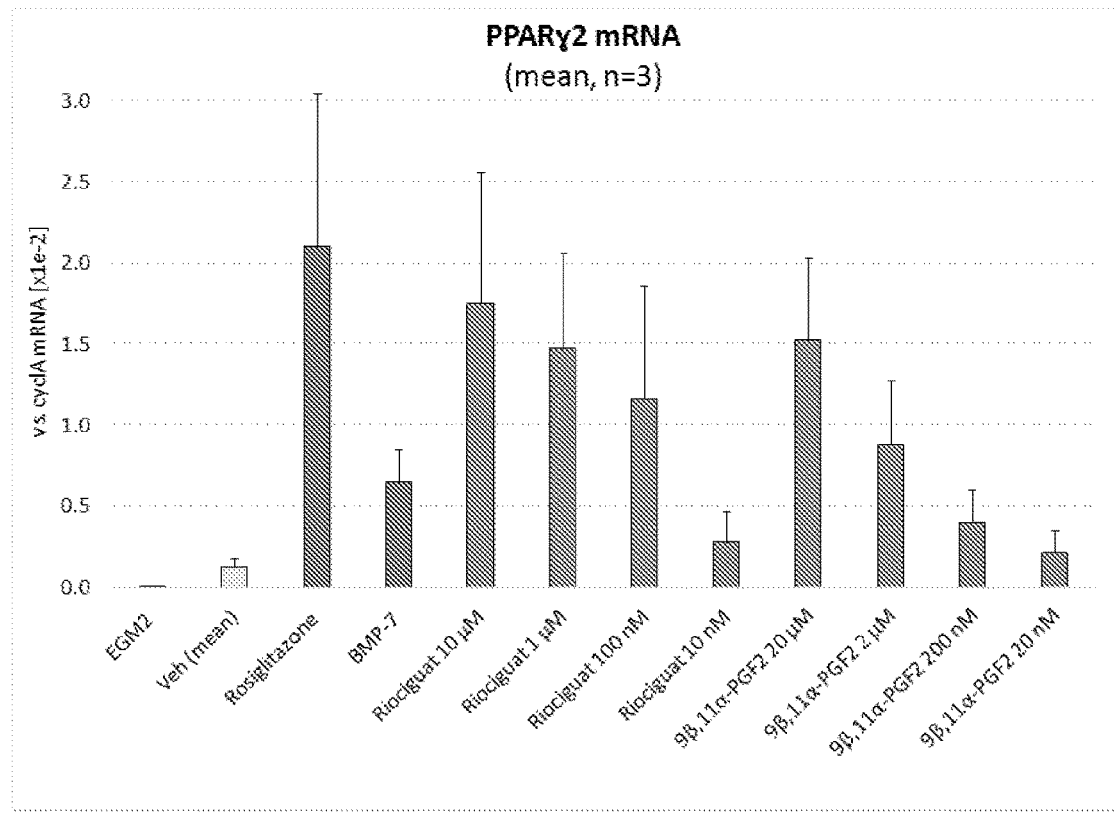
FIG. 7 shows effects of various agents (incubated with brown adipocyte progenitor cells at day-3 to d0) on the expression of PPARγ2 mRNA.
Figure 8:
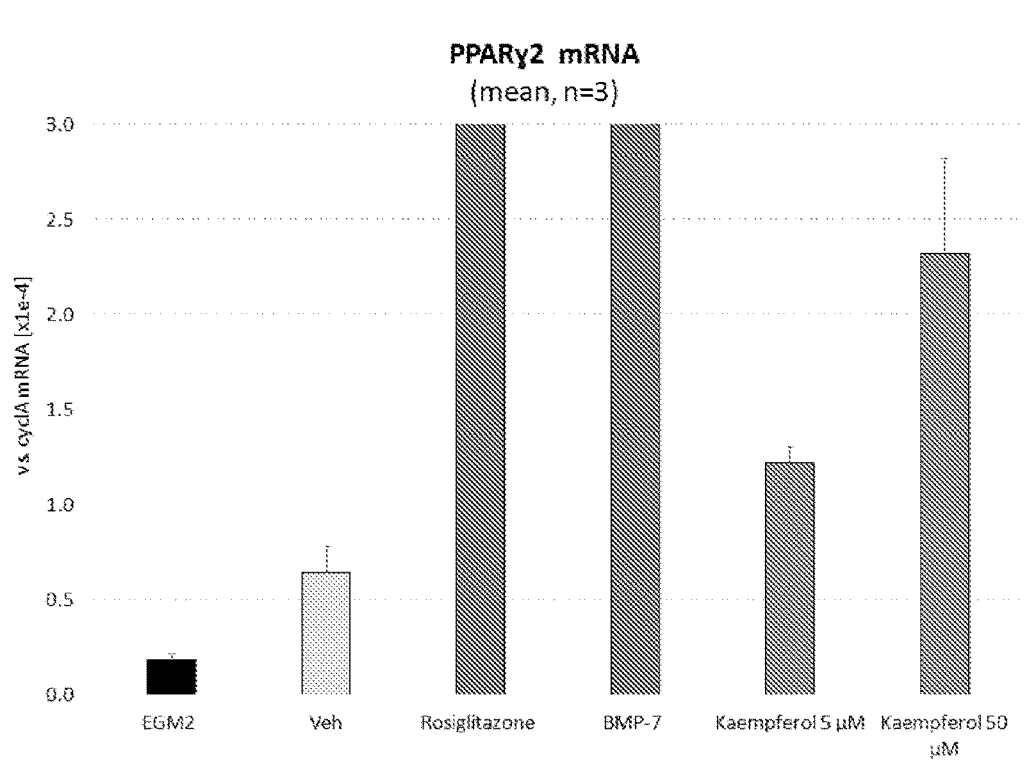
FIG. 8 shows effects of various agents (incubated with brown adipocyte progenitor cells at day-3 to d0 and d0 to d3) on the expression of PPARγ2 mRNA.
Figure 9:
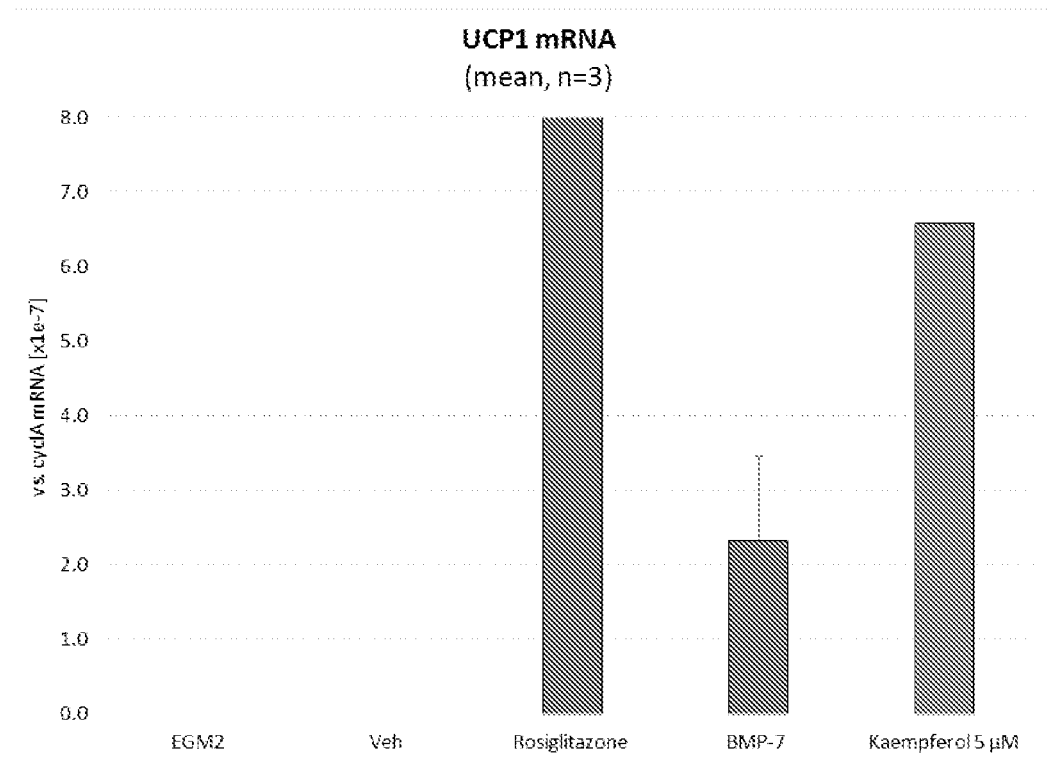
FIG. 9 shows effects of various agents (incubated with brown adipocyte progenitor cells at day-3 to d0 and d0 to d3) on the expression of UCP1 mRNA.
Figure 10:
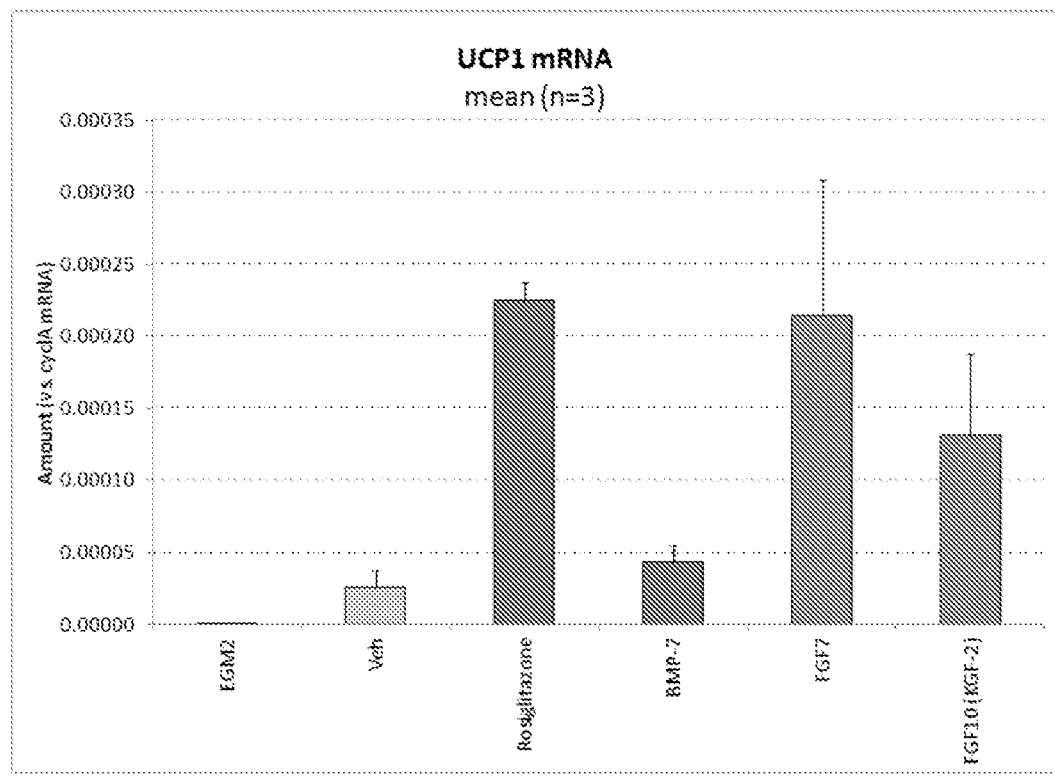
FIG. 10 shows effects of FGF7 and FGF10 (both 100 nM, incubated with brown adipocyte progenitor cells at day-3 to d0 and d0 to d3) on the expression of UCP1 mRNA.
Figure 11:
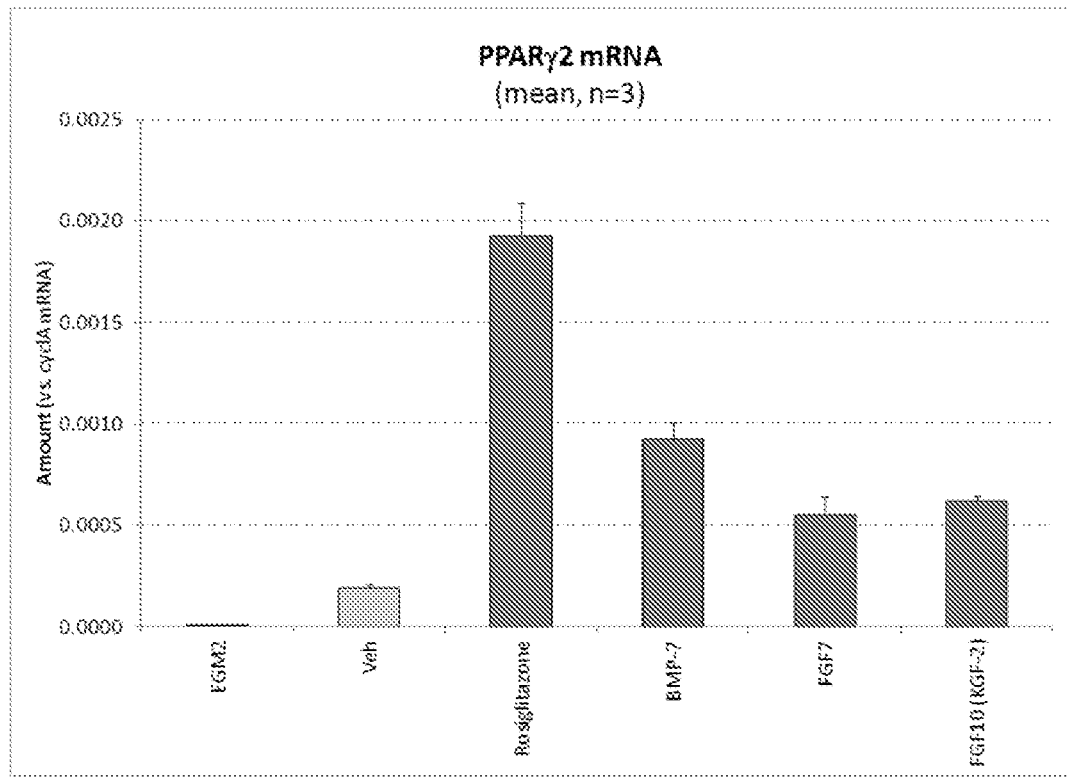
FIG. 11 shows effects of FGF7 and FGF10 (both 100 nM, incubated with brown adipocyte progenitor cells at day-3 to d0 and d0 to d3) on the expression of PPARγ2 mRNA.
Figure 12:
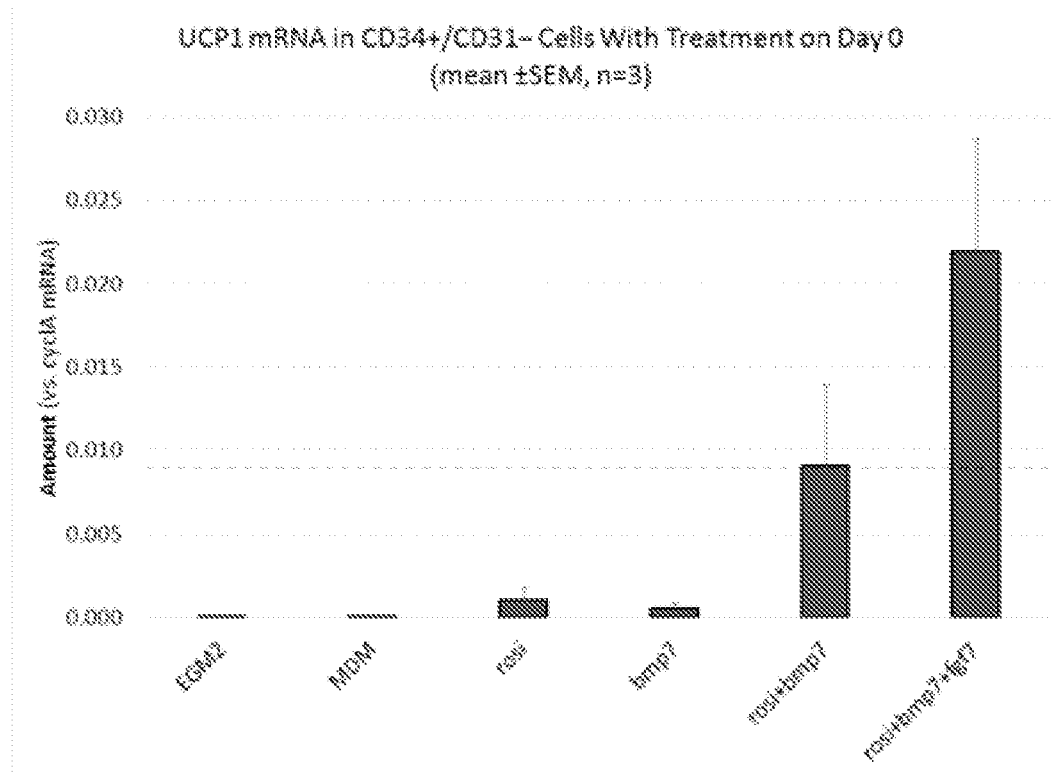
FIG. 12 shows effects of FGF7 (1 nM, incubated with brown adipocyte progenitor cells at day 0 to d3) on the expression of UCP1 mRNA. Rosiglitazone (rosi, 1 μM), bone morphogenic protein-7 (bmp7, 6 nM) or both rosi and bmp7 were incubated with the cells at day-3 to d0.
Figure 13:
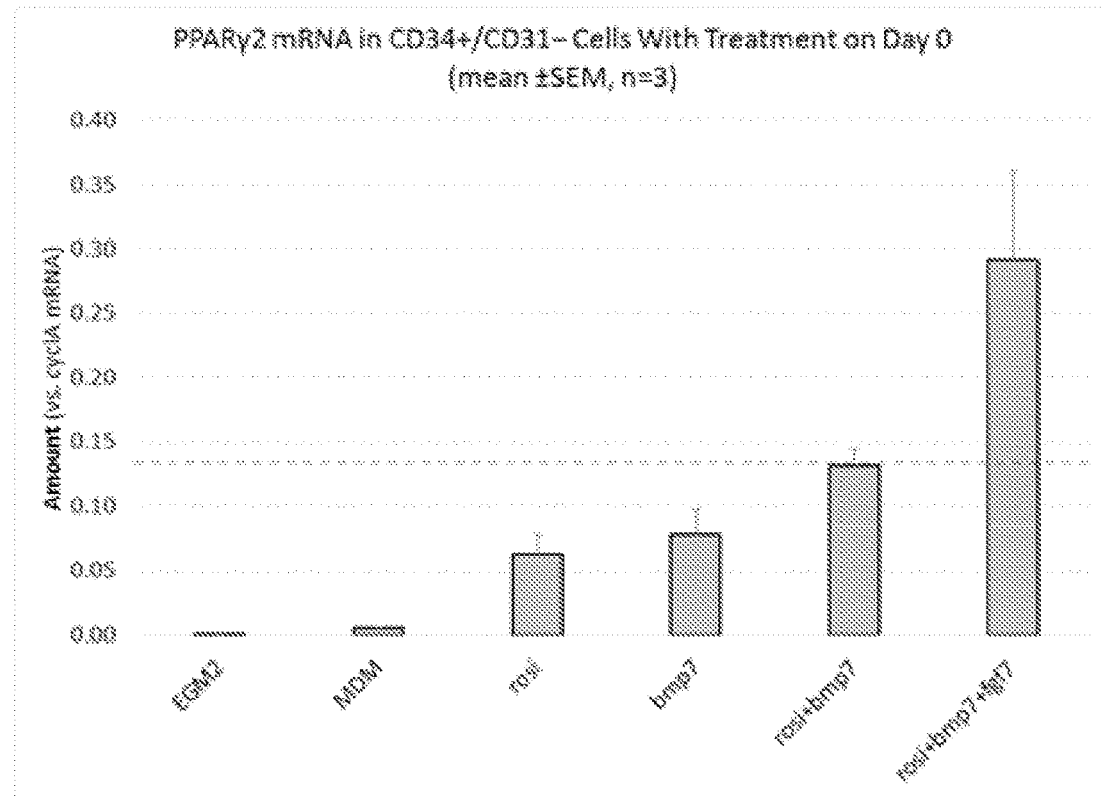
FIG. 13 shows effects of FGF7 (1 nM, incubated with brown adipocyte progenitor cells at day 0 to d3) on the expression of PPARγ2 mRNA. Rosiglitazone (rosi, 1 μM), bone morphogenic protein-7 (bmp7, 6 nM) or both rosi and bmp7 were incubated with the cells at day-3 to d0.
Figure 14:
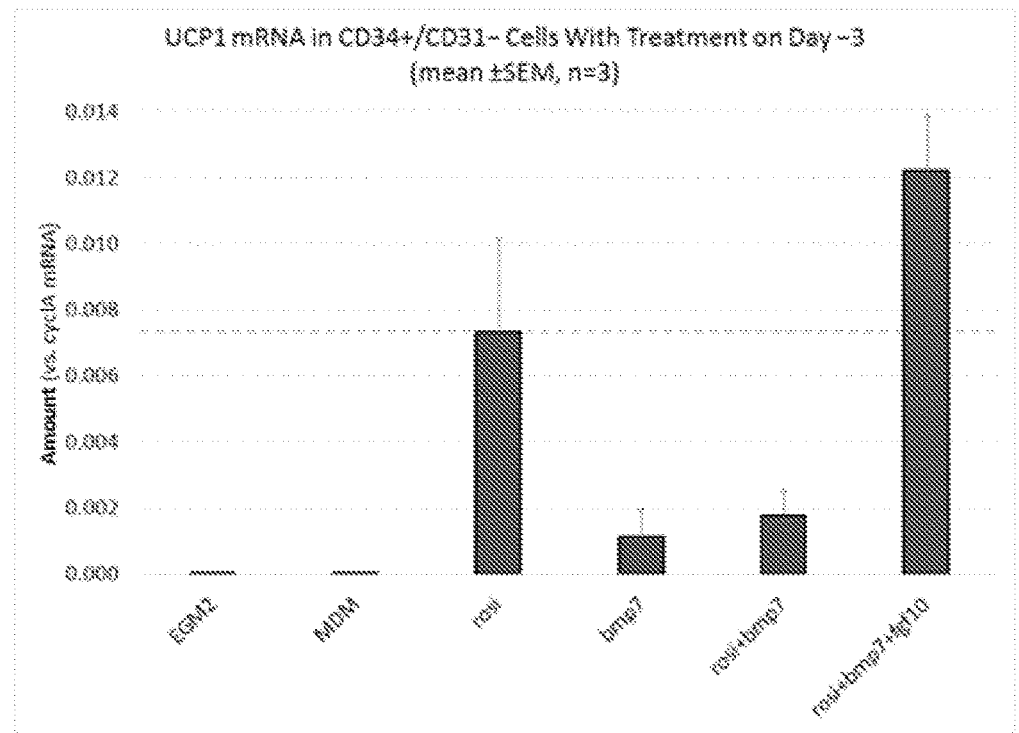
FIG. 14 shows effects of FGF10 (10 nM, incubated with brown adipocyte progenitor cells at day-3 to d0) on the expression of UCP1 mRNA. Rosiglitazone (rosi, 1 μM), bone morphogenic protein-7 (bmp7, 6 nM) or both rosi and bmp7 were incubated with the cells at day-3 to d0.
Figure 15:
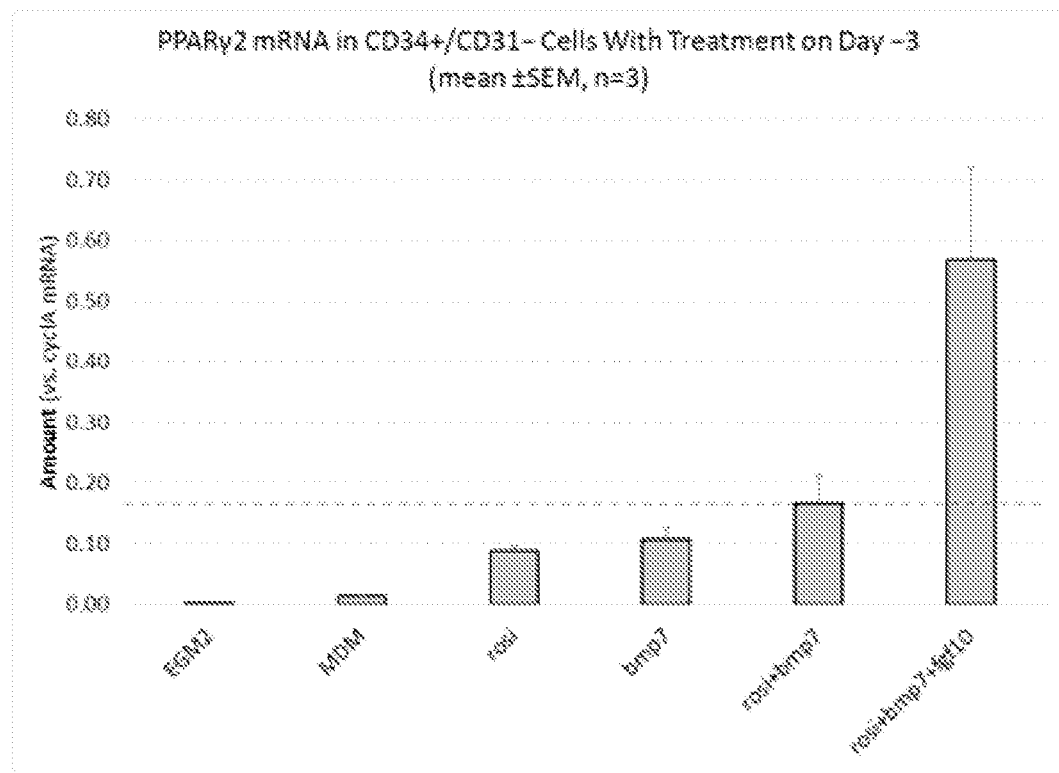
FIG. 15 shows effects of FGF10 (10 nM, incubated with brown adipocyte progenitor cells at day-3 to d0) on the expression of PPARγγ2 mRNA. Rosiglitazone (rosi, 1 μM), bone morphogenic protein-7 (bmp7, 6 nM) or both rosi and bmp7 were incubated with the cells at day-3 to d0.
Figure 16:
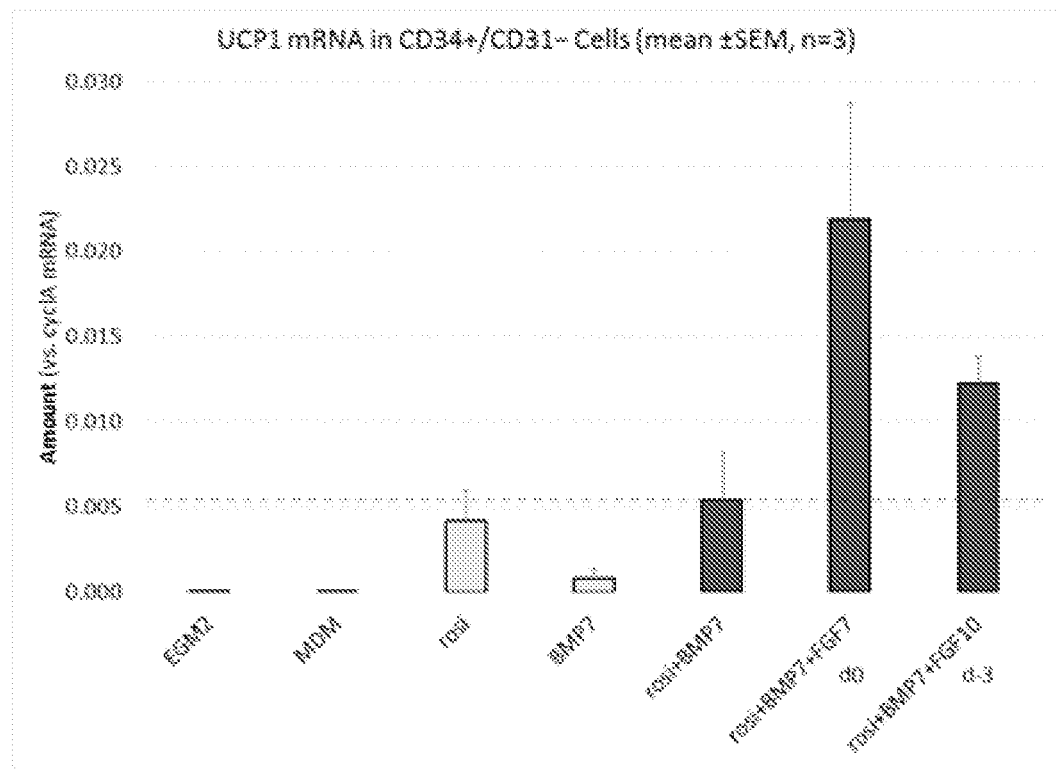
FIG. 16 shows effects of FGF7 (1 nM, incubated with brown adipocyte progenitor cells at day 0 to d3) or FGF10 (10 nM, incubated with the cells at day-3 to d0) on the expression of UCP1 mRNA. Rosiglitazone (rosi, 1 μM), bone morphogenic protein-7 (bmp7, 6 nM) or both rosi and bmp7 were incubated with the cells at day-3 to d0.
Figure 17:
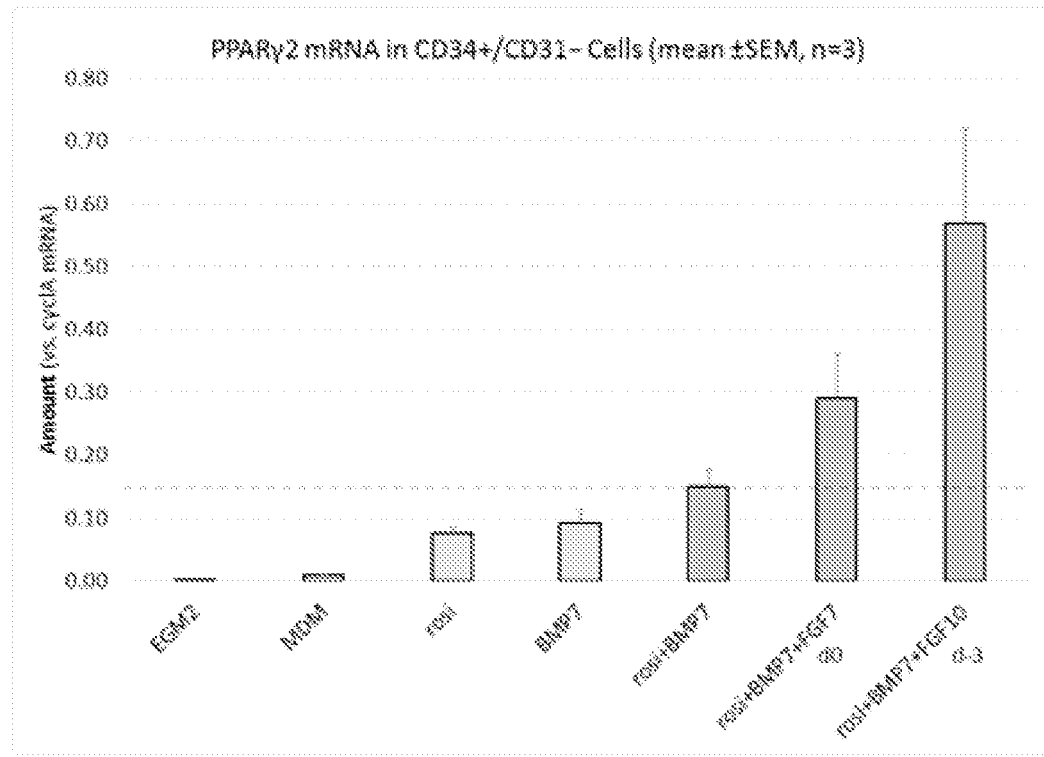
FIG. 17 shows effects of FGF7 (1 nM, incubated with brown adipocyte progenitor cells at day 0 to d3) or FGF10 (10 nM, incubated with the cells at day-3 to d0) on the expression of PPARγ2 mRNA. Rosiglitazone (rosi, 1 μM), bone morphogenic protein-7 (bmp7, 6 nM) or both rosi and bmp7 were incubated with the cells at day-3 to d0.
Figure 18:
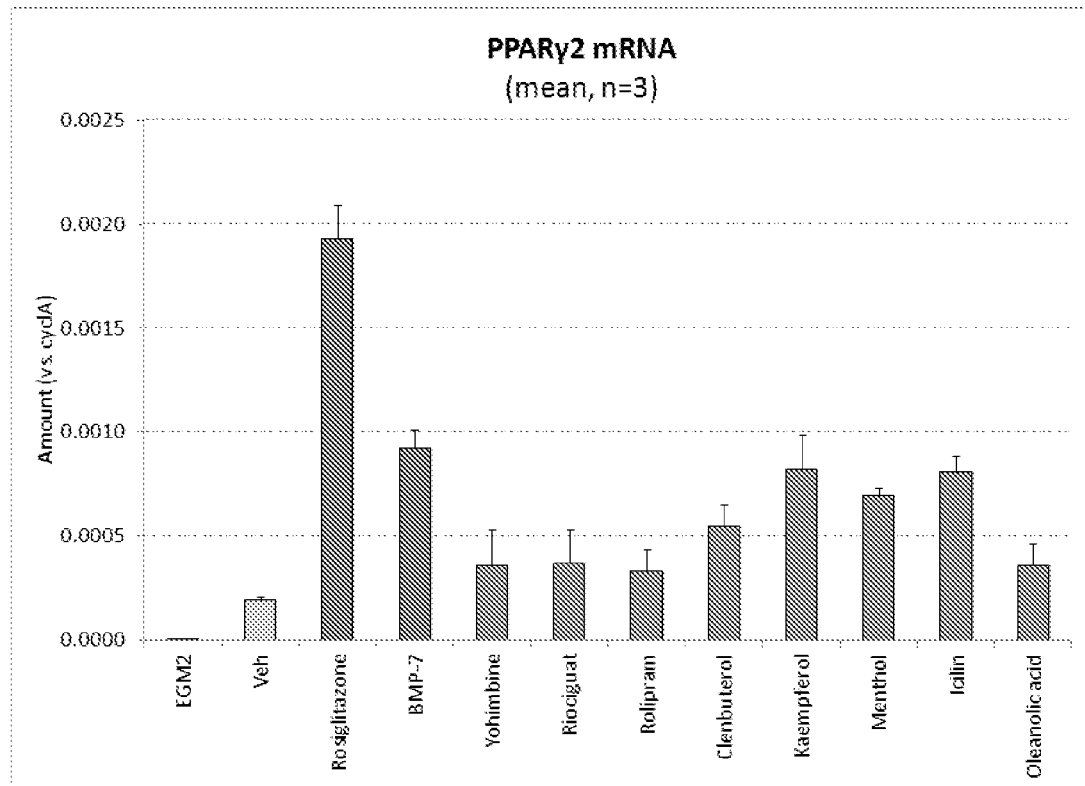
FIG. 18 shows effects of various agents (incubated with brown adipocyte progenitor cells at day-3 to d0 and d0 to d3) on the expression of PPARγ2 mRNA.
Figure 19:
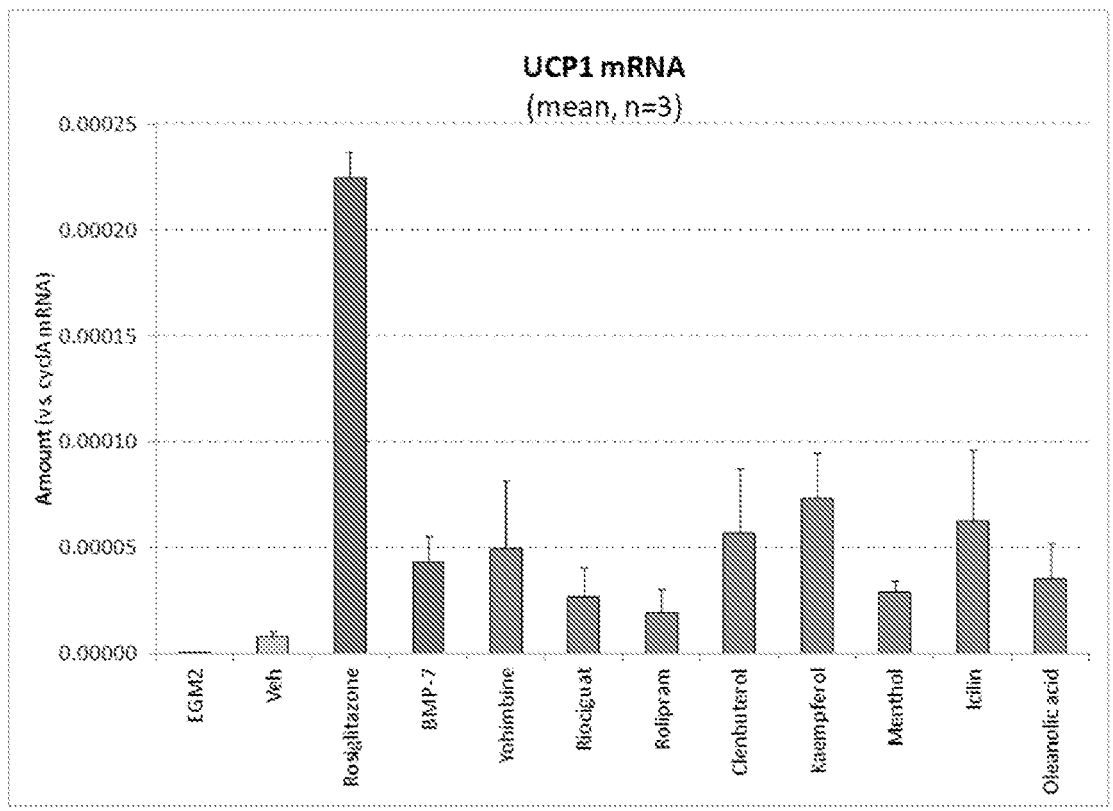
FIG. 19 shows effects of various agents (incubated with brown adipocyte progenitor cells at day-3 to d0 and d0 to d3) on the expression of UCP1 mRNA.
Figure 20A:
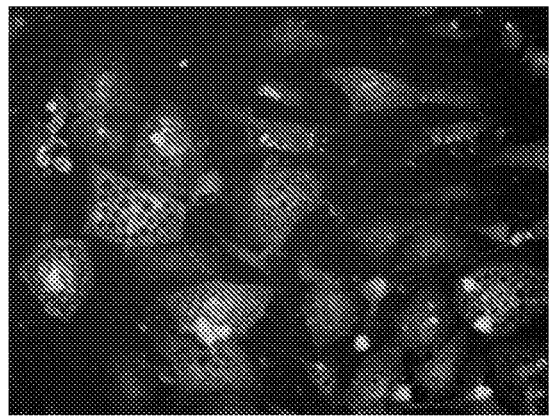
FIGS. 20A-20C show fluorescence microscopy pictures illustrating the immmunohistochemistry (IHC) assay results for UCP1 protein expression (FITC, green) and cell nuclei numbers (DAPI, blue). CD31-cells differentiated for 8 days in minimal differentiation medium (MDM) after exposure to rosiglitazone (1 μM) differentiate profoundly into brown adipocytes expressing high levels of UCP1 (FIG. 20A), whereas cells not exposed to rosiglitazone show a much lower level of differentiation and UCP1 expression (FIG. 20B). Cells maintained in proliferation medium (EGM-2) do not differentiate and express no UCP1 (FIG. 20C).
Figure 20B:
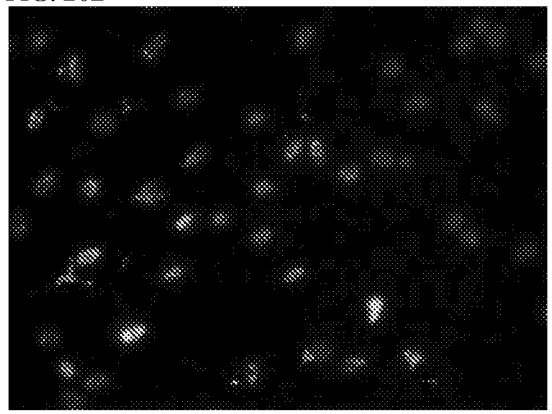
Figure 20C:
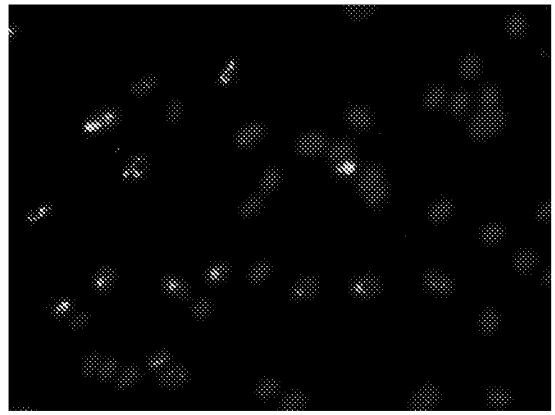
Figure 21:
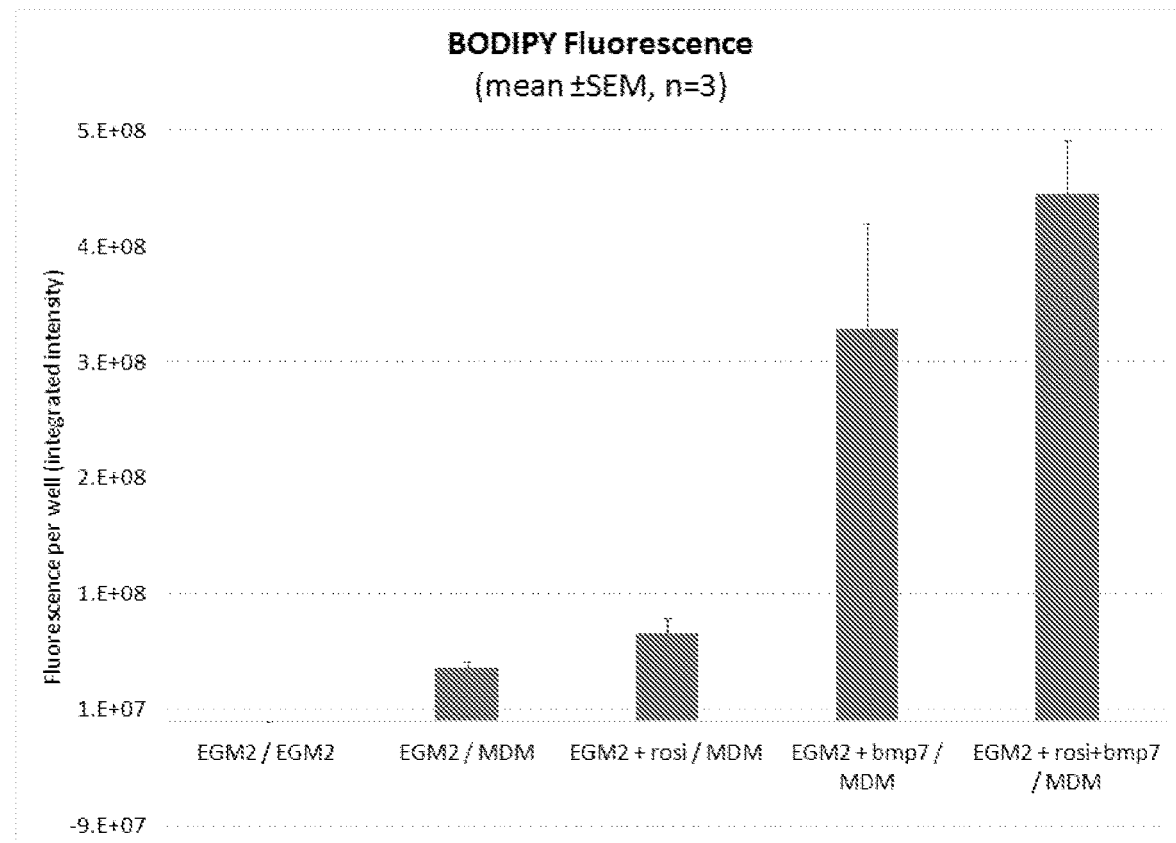
FIG. 21 shows BODIPY 500/510 C1, C12 fluorescence signal after brown adipocyte progenitor cells were induced to differentiate in culture for 9 days in various conditions (rosi and BMP-7 were used from day-3 to d0).
Figure 22:
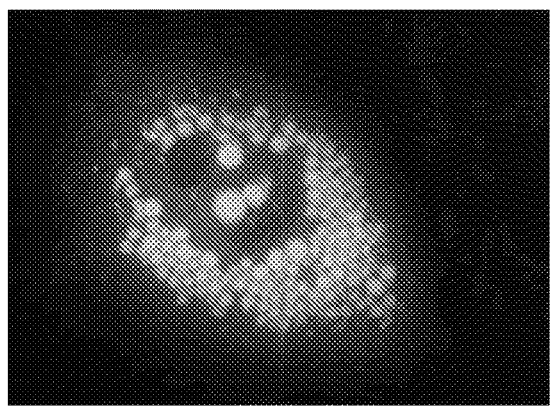
FIG. 22 shows fluorescence microscopy illustrating the BODIPY assay results for intracellular lipid droplet formation (BODIPY 500/510 C1, C12, green). CD31-cells were differentiated for 8 days in minimal differentiation medium (MDM) after exposure to rosiglitazone (1 μM) for 3 days (day-3 to day 0).
Figure 23A:
FIGS. 23A-23H show light microscopic photos of the CD31-cells and resulting brown adipocyte differentiation following treatment with several agents that promote brown adipocyte formation.
Figure 23B:
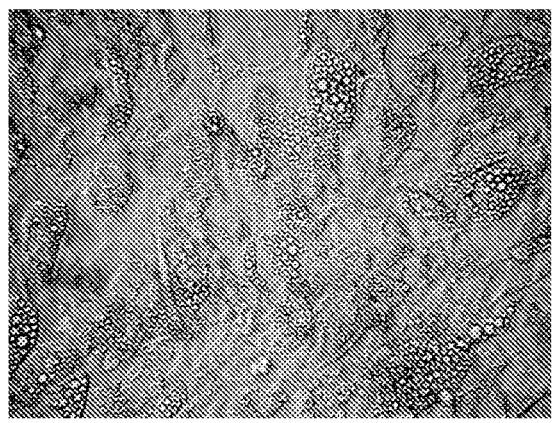
Figure 23C:
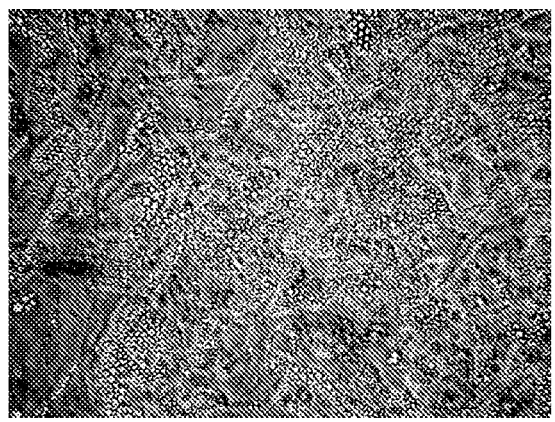
Figure 23D:
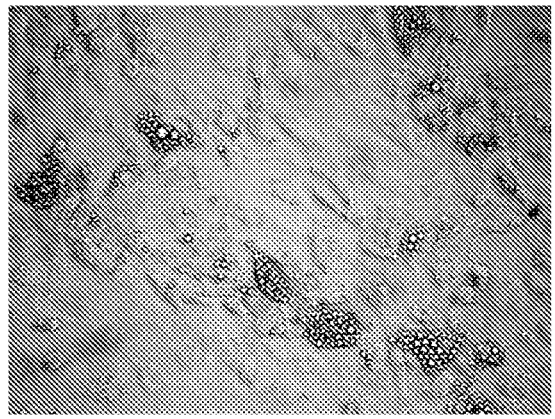
Figure 23E:
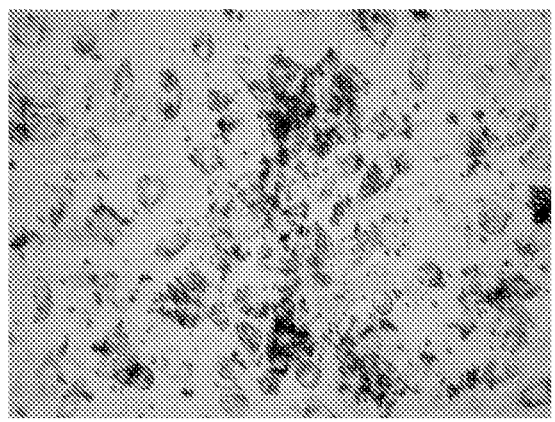
Figure 23F:
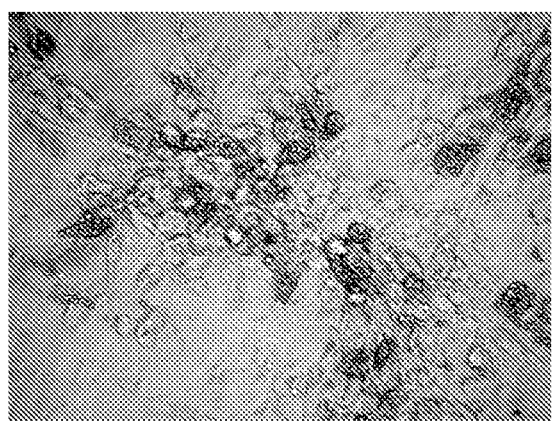
Figure 23G:
Figure 23H:
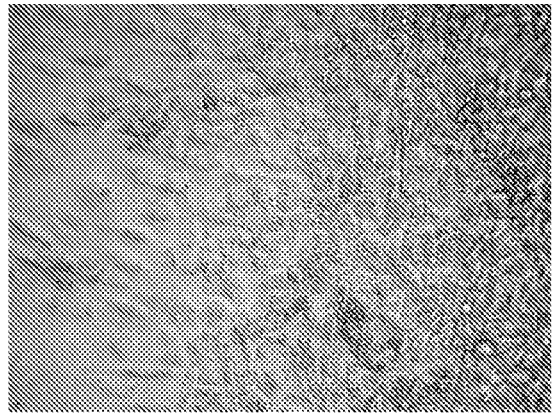

For example, a PPARγ ligand like rosiglitazone can be used to promote the differentiation of CD31-progenitor cells into brown adipocytes (FIGS. 1-19, 20A, 21, 22). Another example is the use of the recombinant protein, human BMP-7 (FIGS. 1-19, 21).

A robust method, previously disclosed in WO2013071063 and incorporated herein by reference, was used for detection of CD31-cell differentiation into brown adipocytes by simultaneously quantifying mRNA species corresponding to the brown adipocyte marker UCP1, the adipocyte marker PPARγ2, and the "housekeeping" gene cyclophilin A which was used as the internal control.

This method permits analysis of a large number of samples to identify agents that enhance the differentiation of CD31-cells into brown adipocytes. When differentiated into brown adipocytes CD31-cells express much higher levels of UCP1 and PPARγ2 mRNA for a given level of cyclophilin A. UCP1 and PPARγ2 mRNA levels normalized to cyclophilin A mRNA levels give an indication of the level of differentiation of the CD31-cells into brown adipocytes, independent of the total number of cells in the sample.

Quantification of UCP1, PPARγ2 and cyclophilin A mRNA by multiplexed TaqMan real-time PCR was thus used to quantify differentiation of the CD31-cells into brown adipocytes.

Using this method the following agents were identified or confirmed to promote the differentiation of BAT progenitor cells into brown adipocytes and/or induce the expression of UCP1, FABP4 (aP2), PPARγ2, mtTFA, PGC-1α, and/or COX IV in BAT progenitor cells in vitro, in vivo, or both: a PPARγ ligand like rosiglitazone, a PDE3 inhibitor like siguazodan, a PDE4 inhibitor like rolipram, a derivative of prostaglandin F2 (PGF2) like 9β,11α-prostaglandin F2, a pepdide derived from the Pituitary adenylate cyclase-activating polypeptide (PACAP, ADCYAP1, UniProt P18509) gene like the PACAP Propeptide of 55 aa (aa 25-79), BDNF (brain-derived neurotrophic factor), a TGR5 agonist like oleanolic acid, BMP-7, kaempferol (KMP, CAS number 520-18-3), a stimulator of soluble guanylate cyclase (sGC) like riociguat (BAY 63-2521, CAS 625115-55-1), FGF7 (fibroblast growth factor-7, KGF, keratinocyte growth factor), FGF10 (fibroblast growth factor-10, KGF-2, keratinocyte growth factor-2), BNP (b-type natriuretic peptide), a TRPM8 (CMRI) ligand like menthol or icilin, bombesin, CNTF (ciliary neurotrophic factor), interleukin-6 (IL-6), orexin B, SDF-1γ (CXCL12), and FGF13 (fibroblast growth factor-13).

Except otherwise indicated, all organic and inorganic chemicals of analytical or molecular biology grade were purchased from Sigma Chemical Co. (St Louis, Mich.), Life Technologies (Grand Island, N.Y.), GenScript, Prospec, LifeTein, AnaSpec. Rosiglitazone was purchased from Cayman Chemical (#71742) and recombinant human BMP7 (rhBMP7) was from R&D Systems (100 µg/ml, 6.3 µM, #354-BP-010).

Cell Culture

Cells were seeded at 10,000 per cm$^2$ in 0.2% gelatin coated plates (48-well tissue culture, Chemglass #CLS-3500-048), cultured until confluency (2-4 days) at 37° C. in Endothelial cell growth medium-2 (EGM2) (BulletKit growth medium, Lonza #CC-3162) and until differentiation (10-16 more days). After 2 or 3 days in EGM2 medium the cells were induced to differentiate by replacing the medium with an adipogenic medium, which is a modification of the adipogenic medium described by Rodriguez et al. [21] and may or may not contain a differentiation inducing agent (e.g., PPARγ agonist). The MDM described above contains:

DMEM/Ham's F-12 50/50 Mix (3.151 g/l, 17.5 mM D-glucose, 3.651 g/l L-glutamine) (Cellgro #10-090-CV), 5 µg/ml (0.86 µM) insulin, 1 µM dexamethasone, 100 µM 3-isobutyl-1-methylxanthine, 0.2 nM 3,3',5-triiodo-L-thyronine, 10 µg/ml (127 nM) transferrin, and 1% penicillin-streptomycin. If rosiglitazone is used as a differentiation-inducing agent, it can be supplied at 1 µM or any other concentration sufficient to induce differentiation of BAT progenitor cells into adipocytes.

For cell expansion studies, confluent cells grown in EGM2 medium only were detached by treatment with trypsin-EDTA for 3-5 min at 37° C., and then split 1:3 or 1:4 and cultured as described above.

Quantification of UCP1 and PPARγ2 mRNA by Quantitative Reverse Transcription, Real-Time PCR Total RNA was prepared from cells using PureLink RNA Isolation Kit (Invitrogen #12183-016) First strand cDNA were synthesized using the High Capacity cDNA Reverse Transcription kit (Applied Biosystems, Foster City, Calif.) and random primers.

Quantitative real-time PCR was performed using an Applied Biosystems StepOnePlus™ instrument, TaqMan Gene Expression Master Mix (Applied Biosystems #4369016), and custom TaqMan gene expression probes and primers for human uncoupling protein-1 "UCP1" (GenBank NM_021833) and for human peptidylprolyl isomerase A "cyclophilin A" (GenBank NM_021130). Custom TaqMan Gene Expression reagents were also developed for simultaneous measurement of peroxisome proliferator-activated receptor gamma, transcript variant 2 (PPARγ2) (GenBank NM_015869) in a multiplexed fashion (with UCP1 and cyclophilin A): UCP1 FAM-MGB probe: TCA AGG GGT TGG TAC CTT CC (SEQ ID NO.: 1), sense primer: CAC TAA CGA AGG ACC AAC GG (SEQ ID NO.: 2), and antisense primer: TTC CAG GAT CCA AGT CGC AA (SEQ ID NO.: 3). Cyclophilin A NED-MGB probe: ACT GCC AAG ACT GAG TGG TT (SEQ ID NO.: 4), sense primer: CAA ATG CTG GAC CCA ACA CA (SEQ ID NO.: 5), and antisense primer: TCA CTT TGC CAA ACA CCA CA (SEQ ID NO.: 6). PPARg2 VIC-MGB probe: TCA CAA GAA ATG ACC ATG GTT G (SEQ ID NO.: 7), sense primer: AGC GAT TCC TTC ACT GAT ACA C (SEQ ID NO.: 8), and antisense primer: CCA GAA TGG CAT CTC TGT GT (SEQ ID NO.: 9).

Cyclophilin A was used as a control to account for any variations due to the efficiency of reverse transcription. Arbitrary units were determined by normalizing target mRNA levels to cyclophilin A mRNA levels (based on Cts).

Statistical Analysis

Data are expressed as means±SEM. Significances were evaluated using the unpaired Student's t-test. Significances were set at p<0.05.

Pictures for Cell Morphology

Pictures of cells were taken using a hand-held digital camera (Nikon Coolpix 950) and inverted microscope (Nikon TMS) used for cell culture observations; images were optimized using Adobe Photoshop Elements 8 functions for Auto Contrast and Auto Levels.

The section headings and subheadings used in this specification are for organizational purposes only and are not to be construed as limiting the subject matter described in any way. Further, while the present teachings are described in conjunction with various embodiments, it is not intended that the present teachings be limited to such embodiments. On the contrary, the present teachings encompass various alternatives, modifications, and equivalents as will be appreciated by those of skill in the art.

Quantification of UCP1 Protein

Differentiation of brown adipocyte progenitors into brown adipocytes can be detected through quantification of UCP1 protein by immunohistochemistry (IHC).

Culturing and differentiation of CD31-cells into brown adipocytes were performed using adipogenic differentiation medium lacking (Minimal Differentiation Medium, MDM) or containing 1 µM rosiglitazone (Reference Differentiation Medium, RDM). After 15 days of differentiation cells were fixed with 4% Paraformaldehyde PBS pH 7.4, and incubated with a UCP1 antibody (Abcam ab23841) and Alexafluor 488 goat anti-rabbit antibody to quantify relative UCP1 levels (green) according to standard protocols. Prior to fixation of cells, nuclei were labeled with 5 µM DAPI (blue) for 10 minutes. Each treatment condition was evaluated in triplicate in a 96-well plate corresponding to approximately 360-480 cells for each data point in total. The InCell 1000 Developer Toolbox software was used to develop an automated cell detection script to measure UCP1 signal intensity, using the nuclei and cytoplasm detection algorithms. As a readout, total intensity of UCP1 signal within the cell was used, normalized to cell number.

In some embodiments, agents or combinations thereof that were identified using this technique include Famotidine, Tiapride hydrochloride, Guanfacine hydrochloride, Reserpine, Minoxidil, Spiperone, Diflunisal, Syrosingopine, Probenecid, Metformin, Thiethylperazine, Colchicine, and Felodipine.

Detection of Brown Adipocyte Differentiation

BODIPY fluorescent dye-labeled neutral lipids become incorporated in cytoplasmic lipid droplets allowing analysis of cellular fatty acid uptake and adipocyte differentiation by fluorescent cellular imaging. Cells are incubated with C1-BODIPY® 500/510 C12 (Molecular Probes #D-3823) for 3 to 6 hours before imaging on a microplate-based high-throughput, high-content, brightfield and fluorescence cellular imager and analyzer (Cyntellect Celigo® or GE Healthcare IN Cell Analyzer).

OTHER EMBODIMENTS

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The present disclosure provides among other things novel compositions capable of recruiting brown adipocytes in vitro and in vivo. While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

INCORPORATION BY REFERENCE

All publications, patents and patent applications referenced in this specification are incorporated herein by reference in their entirety for all purposes to the same extent as if each individual publication, patent or patent application were specifically indicated to be so incorporated by reference.

REFERENCES

[1] M. Klingenspor, Cold-induced recruitment of brown adipose tissue thermogenesis, Exp Physiol. 88 (2003) 141-148.

[2] B. Cannon, J. Nedergaard, The biochemistry of an inefficient tissue: brown adipose tissue, Essays Biochem. 20 (1985) 110-164.

[3] N. J. Rothwell, M. J. Stock, A role for brown adipose tissue in diet-induced thermogenesis, Nature. 281 (1979) 31-35.

[4] B. B. Lowell, V. S-Susulic, A. Hamann, J. A. Lawitts, J. Himms-Hagen, B. B. Boyer, L. P. Kozak, J. S. Flier, Development of obesity in transgenic mice after genetic ablation of brown adipose tissue, Nature 366 (1993) 740-742.

[5] H. M. Feldmann, V. Golozoubova, B. C. M. Cannon, J. Nedergaard, UCP1 ablation induces obesity and abolishes diet-induced thermogenesis in mice exempt from thermal stress by living at thermoneutrality, Cell Metab. 9 (2009) 203-209.

[6] J. Kopecky, G. Clarke, S. Enerback, B. Spiegelman, L. P. Kozak, Expression of the mitochondrial uncoupling protein gene from the aP2 gene promoter prevents genetic obesity, J Clin Invest. 96 (1995).

[7] K. Tsukiyama-Kohara, F. Poulin, M. Kohara, C T. DeMaria, A. Cheng, Z. Wu, A. C. Gingras, A. Katsume, M. Elchebly, B. M. Spiegelman, M. E. Harper, M. L. Tremblay, N. Sonenberg, Adipose tissue reduction in mice lacking the translational inhibitor 4E-BP1, Nature Medicine 7 (2001) 1128-1132.

[8] K. Almind, M. Manieri, W. I. Sivitz, S. Cinti, C R. Kahn, Ectopic brown adipose tissue in muscle provides a mechanism for differences in risk of metabolic syndrome in mice, Proc Natl Acad Sci USA. (2007).

[9] M. Del Mar Gonzalez-Barroso, D. Ricquier, A. M. Cassard-Doulcier, The human uncoupling protein-1 gene (UCP1): present status and perspectives in obesity research, Obes Rev. 1 (2000) 61-72.

[10] B. Cannon, J. Nedergaard, Brown adipose tissue: function and physiological significance, Physiol Rev. 84 (2004) 277-359.

[11] W. D. van Marken Lichtenbelt, J. W. Vanhommerig, N. M. Smulders, J. M. Drossaerts, G. J. Kemerink, N. D. Bouvy, P. Schrauwen, G. J. Teule, Cold-activated brown adipose tissue in healthy men, N Engl J Med. 360 (2009) 1500-1508.

[12] A. M. Cypess, S. Lehman, G. Williams, I. Tal, D. Rodman, A. B. Goldfine, F. C Kuo, E. L. Palmer, Y. H. Tseng, A. Dona, G. M. Kolodny, C R. Kahn, Identification and importance of brown adipose tissue in adult humans, N Engl J Med. 360 (2009) 1509-1517.

[13] K. A. Virtanen, M. E. Lidell, J. Orava, M. Heglind, R. Westergren, T. Niemi, M. Taittonen, J. Laine, N. J. Savisto, S. Enerback, P. Nuutila, Functional brown adipose tissue in healthy adults, N Engl J Med. 360 (2009) 1518-1525.

[14] H. L. Garstka, W. E. Schmitt, J. Schultz, B. Sogl, B. Silakowski, A. Perez-Martos, J. Montoya, R. J. Wiesner, Import of mitochondrial transcription factor A (TFAM) into rat liver mitochondria stimulates transcription of mitochondrial DNA, Nucleic Acids Res. 31 (2003) 5039-5047.

[15] Z. Wu, P. Puigserver, B. M. Spiegelman, Transcriptional activation of adipogenesis, Curr Opin Cell Biol. 11 (1999) 689-694.

[17] L. A. Foellmi-Adams, B. M. Wyse, D. Herron, J. Nedergaard, R. F. Kletzien, Induction of uncoupling protein in brown adipose tissue. Synergy between norepinephrine and pioglitazone, an insulin-sensitizing agent, Biochem Pharmacol. 52 (1996) 693-701.

[18] M. Mensink, M. K. Hesselink, A. P. Russell, G. Schaart, J. P. SeIs, P. Schrauwen, Improved skeletal muscle oxidative enzyme activity and restoration of PGC-I alpha and PPAR beta/delta gene expression upon rosiglitazone treatment in obese patients with type 2 diabetes mellitus, Int J Obes (Lond). 31 (2007) 1302-1310.

[19] L. Lehr, K. Canola, C. Asensio, M. Jimenez, F. Kuehne, J. P. Giacobino, P. Muzzin, The control of UCP1 is dissociated from that of PGC-I alpha or of mitochondriogenesis as revealed by a study using beta-less mouse brown adipocytes in culture, FEBS Lett. 580 (2006) 4661-4666.

[20] O. Champigny, B. R. Holloway, D. Ricquier, Regulation of UCP gene expression in brown adipocytes differentiated in primary culture. Effects of a new beta-adrenoceptor agonist, MoI Cell Endocrinol. 86 (1992) 73-82.

[24] M. Jimenez, C. Yvon, L. Lehr, B. Leger, P. Keller, A. Russell, F. Kuhne, P. Flandin, J. P. Giacobino, P. Muzzin, Expression of uncoupling protein-3 in subsarcolemmal and intermyofibrillar mitochondria of various mouse muscle types and its modulation by fasting, Eur J Biochem. 269 (2002) 2878-2884.

[26] Tseng Y H, Kokkotou E, Schulz T J, Huang T L, Winnay J N, Taniguchi C M, Tran T T, Suzuki R, Espinoza D O, Yamamoto Y, Ahrens M J, Dudley A T, Norris A W, Kulkarni R N, Kahn C R. New role of bone morphogenetic protein 7 in brown adipogenesis and energy expenditure. Nature. 2008 Aug. 21; 454(7207):1000-4. PubMed PMID: 18719589; PubMed Central PMCID: PMC2745972.

[27] Zhang H, Schulz T J, Espinoza D O, Huang T L, Emanuelli B, Kristiansen K, Tseng Y H. Cross talk between insulin and bone morphogenetic protein signaling systems in brown adipogenesis. Mol Cell Biol. 2010 September; 30(17):4224-33. Epub 2010 Jun. 28. PubMed PMID: 20584981; PubMed Central PMCID: PMC2937545.

[28] Schulz T J, Huang T L, Tran T T, Zhang H, Townsend K L, Shadrach J L, Cerletti M, McDougall L E, Giorgadze N, Tchkonia T, Schrier D, Falb D, Kirkland J L, Wagers A J, Tseng Y H. Identification of inducible brown adipocyte progenitors residing in skeletal muscle and white fat. Proc Natl Acad Sci USA. 2011 Jan. 4; 108(1):143-8. Epub 2010 Dec. 20. PubMed PMID: 21173238; PubMed Central PMCID: PMC3017184.

[29] Farmer S R, Boss O (2012) Recruitment of Brown Adipose Tissue as a Therapy for Obesity-Associated Diseases. Frontiers in Endocrinology 3.

[30] Zhang N, Chen W, Zhou X, Xie X, Meng A, et al. (2013) C333H ameliorated insulin resistance through selectively modulating PPARgamma in brown adipose tissue of db/db mice. Biol Pharm Bull.

[31] Yoneshiro T, Aita S, Matsushita M, Kayahara T, Kameya T, et al. (2013) Recruited brown adipose tissue as an antiobesity agent in humans. J Clin Invest.

[32] Vijgen G H, Sparks L M, Bouvy N D, Schaart G, Hoeks J, et al. (2013) Increased Oxygen Consumption in Human Adipose Tissue From the "Brown Adipose Tissue" Region. J Clin Endocrinol Metab.

[33] Vijgen G H, van Marken Lichtenbelt W D (2013) Brown adipose tissue: clinical impact of a re-discovered thermogenic organ. Front Biosci (Elite Ed) E5: 823-833.

[34] van der Lans A A, Hoeks J, Brans B, Vijgen G H, Visser M G, et al. (2013) Cold acclimation recruits human brown fat and increases nonshivering thermogenesis. The Journal of Clinical Investigation 123: 3395-3403.

[35] Stanford K I, Middelbeek R J, Townsend K L, An D, Nygaard E B, et al. (2013) Brown adipose tissue regulates glucose homeostasis and insulin sensitivity. J Clin Invest 123: 215-223.

[36] Pasanisi F, Pace L, Fonti R, Marra M, Sgambati D, et al. (2013) Evidence of Brown Fat Activity in Constitutional Leanness. J Clin Endocrinol Metab.

[37] Yin H, Pasut A, Soleimani V D, Bentzinger C F, Antoun G, et al. (2013) MicroRNA-133 Controls Brown Adipose Determination in Skeletal Muscle Satellite Cells by Targeting Prdm 16. Cell Metab 17: 210-224.

The invention claimed is:

1. A method of promoting brown adipogenesis in a subject in need thereof, the method comprising:
    contacting a cell of a subject having a metabolic disorder with an agent selected from one or more of:
        fibroblast growth factor (FGF) 7 (FGF7); and
        stromal cell-derived factor 1 (SDF-1); and
    transplanting said cell into the subject after said contacting step;
    wherein the cell is a BAT progenitor cell isolated from human skeletal muscle;
    wherein the metabolic disorder is selected from the group consisting of obesity, type II diabetes, insulin resistance, hyperinsulinemia, hypertension, hyperlipidemia, hepatosteatosis, fatty liver, non-alcoholic fatty liver disease, hyperuricemia, polycystic ovarian syndrome, acanthosis nigricans, hyperphagia, triglyceride storage disease, Bardet-Biedl syndrome, Laurence-Moon syndrome, Prader-Willi syndrome, neurodegenerative diseases, and/or Alzheimer's disease.

2. The method of claim 1 wherein the cell is positive for CD34.

3. The method of claim 1 wherein the cell is negative for CD31.

* * * * *